United States Patent
Gege et al.

(10) Patent No.: US 7,691,851 B2
(45) Date of Patent: Apr. 6, 2010

(54) METALLOPROTEASE INHIBITORS CONTAINING A HETEROCYCLIC MOIETY

(75) Inventors: Christian Gege, Mauer (DE); Arthur Taveras, Southborough, MA (US)

(73) Assignee: Alantos Pharmaceuticals Holding, Inc., Thousand Oaks, CA (US)

( * ) Notice: Subject to any disclaimer, the term of this patent is extended or adjusted under 35 U.S.C. 154(b) by 0 days.

(21) Appl. No.: 12/074,994

(22) Filed: Mar. 7, 2008

(65) Prior Publication Data

US 2008/0221091 A1    Sep. 11, 2008

Related U.S. Application Data

(60) Provisional application No. 60/905,565, filed on Mar. 7, 2007.

(51) Int. Cl.
*C07D 498/04* (2006.01)
*A61K 31/5383* (2006.01)

(52) U.S. Cl. .................................. 514/230.2; 544/101
(58) Field of Classification Search .................. 544/101; 514/230.2
See application file for complete search history.

(56) References Cited

U.S. PATENT DOCUMENTS

2007/0155739 A1    7/2007    Sucholeiki et al.

FOREIGN PATENT DOCUMENTS

| EP | 01955697 A1 | 8/2008 |
| JP | 2008511574 A * | 4/2008 |
| WO | WO 2005/105760 A1 | 11/2005 |
| WO | WO 2006024517 A1 * | 3/2006 |
| WO | WO 2006/083454 | 8/2006 |
| WO | WO 2006/093832 A2 | 9/2006 |
| WO | WO 2006/128184 | 11/2006 |
| WO | WO 2007/063925 A2 | 6/2007 |
| WO | WO 2007/079199 | 7/2007 |
| WO | WO 2007/139856 | 12/2007 |
| WO | WO 2008/002671 | 1/2008 |

* cited by examiner

*Primary Examiner*—Kahsay T Habte
(74) *Attorney, Agent, or Firm*—Elsa D. Lemoine

(57) ABSTRACT

The present invention relates generally to pharmaceutical agents containing a heterocyclic moiety, and in particular, to heterocyclic metalloprotease inhibiting compounds. More particularly, the present invention provides a new class of heterocyclic MMP-13 inhibiting compounds with a modified benzoxazine moiety, that exhibit an increased potency and selectivity in relation to currently known MMP-13 inhibitors.

9 Claims, No Drawings

METALLOPROTEASE INHIBITORS CONTAINING A HETEROCYCLIC MOIETY

CROSS REFERENCE TO RELATED APPLICATIONS

This application claims the benefit of U.S. Provisional Application No. 60/905,565, filed Mar. 7, 2007, which is hereby incorporated by reference.

FIELD OF THE INVENTION

The present invention relates generally to metalloprotease inhibiting compounds containing a heterocyclic moiety, and more particularly to MMP-13 inhibiting compounds with a modified benzoxazine moiety.

BACKGROUND OF THE INVENTION

Matrix metalloproteinases (MMPs) and aggrecanases (ADAMTS=a disintegrin and metalloproteinase with thrombospondin motif) are a family of structurally related zinc-containing enzymes that have been reported to mediate the breakdown of connective tissue in normal physiological processes such as embryonic development, reproduction, and tissue remodelling. Over-expression of MMPs and aggrecanases or an imbalance between extracellular matrix synthesis and degradation has been suggested as factors in inflammatory, malignant and degenerative disease processes. MMPs and aggrecanases are, therefore, targets for therapeutic inhibitors in several inflammatory, malignant and degenerative diseases such as rheumatoid arthritis, osteoarthritis, osteoporosis, periodontitis, multiple sclerosis, gingivitis, corneal epidermal and gastric ulceration, atherosclerosis, neointimal proliferation (which leads to restenosis and ischemic heart failure) and tumor metastasis.

The ADAMTSs are a group of proteases that are encoded in 19 ADAMTS genes in humans. The ADAMTSs are extracellular, multidomain enzymes whose functions include collagen processing, cleavage of the matrix proteoglycans, inhibition of angiogenesis and blood coagulation homoeostasis (*Biochem. J.* 2005, 386, 15-27; *Arthritis Res. Ther.* 2005, 7, 160-169; *Curr. Med. Chem. Anti-Inflammatory Anti-Allergy Agents* 2005, 4, 251-264).

The mammalian MMP family has been reported to include at least 20 enzymes (*Chem. Rev.* 1999, 99, 2735-2776). Collagenase-3 (MMP-13) is among three collagenases that have been identified. Based on identification of domain structures for individual members of the MMP family, it has been determined that the catalytic domain of the MMPs contains two zinc atoms; one of these zinc atoms performs a catalytic function and is coordinated with three histidines contained within the conserved amino acid sequence of the catalytic domain. MMP-13 is over-expressed in rheumatoid arthritis, osteoarthritis, abdominal aortic aneurysm, breast carcinoma, squamous cell carcinomas of the head and neck, and vulvar squamous cell carcinoma. The principal substrates of MMP-13 are fibrillar collagens (types I, II, III) and gelatins, proteoglycans, cytokines and other components of ECM (extracellular matrix).

The activation of the MMPs involves the removal of a propeptide, which features an unpaired cysteine residue complexed with the catalytic zinc (II) ion. X-ray crystal structures of the complex between MMP-3 catalytic domain and TIMP-1 and MMP-14 catalytic domain and TIMP-2 also reveal ligation of the catalytic zinc (II) ion by the thiol of a cysteine residue. The difficulty in developing effective MMP inhibiting compounds comprises several factors, including choice of selective versus broad-spectrum MMP inhibitors and rendering such compounds bioavailable via an oral route of administration.

MMP-3 (stromelysin-1; transin-1) is another member of the MMP family (*FASEB J.* 1991, 5, 2145-2154). Human MMP-3 was initially isolated from cultured human synoviocytes. It is also expressed by chondrocytes and has been localized in OA cartilage and synovial tissues (*Am. J. Pathol.* 1989, 135, 1055-64).

MMP-3 is produced by basal keratinocytes in a variety of chronic ulcers. MMP-3 mRNA and Protein were detected in basal keratinocytes adjacent to but distal from the wound edge in what probably represents the sites of proliferating epidermis. MMP-3 may thus prevent the epidermis from healing (*J. Clin. Invest.* 1994, 94, 79-88).

MMP-3 serum protein levels are significantly elevated in patients with early and long-term rheumatoid arthritis (*Arthritis Rheum.* 2000, 43, 852-8) and in osteoarthritis patients (*Clin. Orthop. Relat. Res.* 2004, 428, 272-85) as well as in other inflammatory diseases like systemic lupus erythematosis and ankylosing spondylitis (*Rheumatology* 2006, 45, 414-20).

MMP-3 acts on components of the ECM as aggrecan, fibronectin, gelatin, laminin, elastin, fibrillin and others and on collagens of type III, IV, V, VII, IX, X (*Clin. Orthop. Relat. Res.* 2004, 428, 272-85). On collagens of type II and IX, MMP-3 exhibits telopeptidase activity (*Arthritis Res.* 2001, 3, 107-13; *Clin. Orthop. Relat. Res.* 2004, 427, S118-22). MMP-3 can activate other MMP family members such as MMP-1, MMP-7, MMP-8, MMP-9 and MMP-13 (*Ann. Rheum. Dis.* 2001, 60 Suppl 3:iii62-7).

MMP-3 is involved in the regulation of cytokines and chemokines by releasing TGFβ1 from the ECM, activating TNFα, inactivating IL-1β and releasing IGF (*Nat. Rev. Immunol.* 2004, 4, 617-29). A potential role for MMP-3 in the regulation of macrophage infiltration is based on the ability of the enzyme to convert active MCP species into antagonistic peptides (*Blood* 2002, 100, 1160-7).

MMP-8 (collagenase-2; neutrophil collagenase; EC 3.4.24.34) is another member of the MMP family (*Biochemistry* 1990, 29, 10628-34). Human MMP-8 was initially located in human neutrophils (*Biochemistry* 1990, 29, 10620-7). It is also expressed by macrophages, human mucosal keratinocytes, bronchial epithelial cells, ginigival fibroblasts, resident synovial and articular chondrodrocytes mainly in the course of inflammatory conditions (*Cytokine & Growth Factor Rev.* 2006, 17, 217-23).

The activity of MMP-8 is tightly regulated and mostly limited to the sites of inflammation. MMP-8 is expressed and stored as an inactive pro-enzyme in the granules of the neutrophils. Only after the activation of the neutrophils by proinflammatory mediators, MMP-8 is released and activated to exert its function.

MMP-8 plays a key role in the migration of immune cells to the sites of inflammation. MMP-8 degrades components of the extracellular matrix (ECM) such as collagen type I, II, III, VII, X, cartilage aggrecan, laminin-5, nidogen, fibronectin, proteoglycans and tenascin, thereby facilitating the cells migration through the ECM barrier. MMP-8 also influences the biological activity of its substrates. Through proteolytic processing of the chemokines IL-8, GCP-2, ENA-78, MMP-8 increases the chemokines ability to activate the infiltrating immune cells. While MMP-8 inactivates the serine protease inhibitor alpha-1 antitrypsin through its cleavage (*Eur. J. Biochem.* 2003, 270, 3739-49; *PloS One* 2007, 3, 1-10; *Cytokine & Growth Factor Rev.* 2006, 17, 217-23).

MMP-8 has been implicated in the pathogenesis of several chronic inflammatory diseases characterized by the excessive influx and activation of neutrophils, including cystic fibrosis (*Am. J. Resprir. Critic. Care Med* 1994, 150, 818-22), rheumatoid arthritis (*Clin. Chim. Acta* 1996, 129-43), chronic periodontal disease (*Annals Med.* 2006, 38, 306-321) and chronic wounds (*J. Surg. Res.* 1999, 81, 189-195).

In osteoarthritis patients, MMP-8 protein expression is significantly elevated in inflamed human articular cartilage in the knee and ankle joints (*Lab Invest.* 1996, 74, 232-40; *J. Biol. Chem.* 1996, 271, 11023-6).

The levels of activated MMP-8 in BALF is an indicator of the disease severity and correlates with the airway obstruction in patients with asthma, COPD, pulmonary emphysema and bronchiectasis (*Lab Invest.* 2002, 82, 1535-45; *Am. J. Respir. Crit. Care Med.* 1999, 159, 1985-91; *Respir. Med.* 2005, 99, 703-10; *J. Pathol.* 2001, 194, 232-38).

SUMMARY OF THE INVENTION

The present invention relates to a new class of heterocyclic moiety containing pharmaceutical agents which inhibits metalloproteases. In particular, the present invention provides a new class of metalloprotease inhibiting compounds that exhibit potent inhibiting activity towards metalloproteases, in particular towards MMP-13.

The present invention provides a new classes of heterocyclic metalloprotease compounds, which is represented by the following general formula:

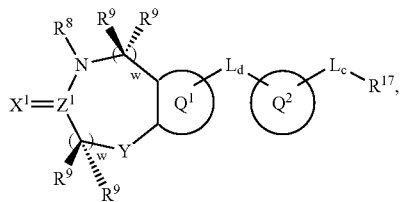

Formula (I)

wherein all variables in the preceding Formulas (I) are as defined hereinbelow.

The heterocyclic metalloprotease inhibiting compounds of the present invention may be used in the treatment of metalloprotease mediated diseases, such as rheumatoid arthritis, osteoarthritis, abdominal aortic aneurysm, cancer (e.g. but not limited to melanoma, gastric carcinoma or non-small cell lung carcinoma), inflammation, atherosclerosis, multiple sclerosis, chronic obstructive pulmonary disease, ocular diseases (e.g. but not limited to ocular inflammation, glaucoma, retinopathy of prematurity, macular degeneration with the wet type preferred and corneal neovascularization), neurologic diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimers disease, arterial plaque formation, oncology, periodontal, viral infection, stroke, atherosclerosis, cardiovascular disease, reperfusion injury, trauma, chemical exposure or oxidative damage to tissues, chronic wound healing, wound healing, hemorrhoid, skin beautifying, pain, inflammatory pain, bone pain and joint pain, acne, acute alcoholic hepatitis, acute inflammation, acute pancreatitis, acute respiratory distress syndrome, adult respiratory disease, airflow obstruction, airway hyperresponsiveness, alcoholic liver disease, allograft rejections, angiogenesis, angiogenic ocular disease, arthritis, asthma, atopic dermatitis, bronchiectasis, bronchiolitis, bronchiolitis obliterans, burn therapy, cardiac and renal reperfusion injury, celiac disease, cerebral and cardiac ischemia, CNS tumors, CNS vasculitis, colds, contusions, cor pulmonae, cough, Crohn's disease, chronic bronchitis, chronic inflammation, chronic pancreatitis, chronic sinusitis, crystal induced arthritis, cystic fibrosis, delayed type hypersensitivity reaction, duodenal ulcers, dyspnea, early transplantation rejection, emphysema, encephalitis, endotoxic shock, esophagitis, gastric ulcers, gingivitis, glomerulonephritis, glossitis, gout, graft vs. host reaction, gram negative sepsis, granulocytic ehrlichiosis, hepatitis viruses, herpes, herpes viruses, HIV, hypercapnea, hyperinflation, hyperoxia-induced inflammation, hypoxia, hypersensitivity, hypoxemia, inflammatory bowel disease, interstitial pneumonitis, ischemia reperfusion injury, kaposi's sarcoma associated virus, liver fibrosis, lupus, malaria, meningitis, multi-organ dysfunction, necrotizing enterocolitis, osteoporosis, chronic periodontitis, periodontitis, peritonitis associated with continuos ambulatory peritoneal dialysis (CAPD), pre-term labor, polymyositis, post surgical trauma, pruritis, psoriasis, psoriatic arthritis, pulmatory fibrosis, pulmatory hypertension, renal reperfusion injury, respiratory viruses, restinosis, right ventricular hypertrophy, sarcoidosis, septic shock, small airway disease, sprains, strains, subarachnoid hemorrhage, surgical lung volume reduction, thrombosis, toxic shock syndrome, transplant reperfusion injury, traumatic brain injury, ulcerative colitis, vasculitis, ventilation-perfusion mismatching, and wheeze.

In particular, the heterocyclic metalloprotease inhibiting compounds of the present invention may be used in the treatment of MMP-13, MMP-8 and MMP-3 mediated degenerative diseases characterized by excessive extracellular matrix degradation and/or remodelling, such as cancer, and chronic inflammatory diseases such as arthritis, rheumatoid arthritis, osteoarthritis, atherosclerosis, abdominal aortic aneurysm, inflammation, multiple sclerosis, parkinsons disease, chronic obstructive pulmonary disease and pain, such as inflammatory pain, bone pain and joint pain.

The present invention also provides heterocyclic metalloprotease inhibiting compounds that are useful as active ingredients in pharmaceutical compositions for treatment or prevention of metalloprotease—especially MMP-13—mediated diseases. The present invention also contemplates use of such compounds in pharmaceutical compositions for oral or parenteral administration, comprising one or more of the heterocyclic metalloprotease inhibiting compounds disclosed herein.

The present invention further provides methods of inhibiting metalloproteases, by administering formulations, including, but not limited to, oral, rectal, topical, intravenous, parenteral (including, but not limited to, intramuscular, intravenous), ocular (ophthalmic), transdermal, inhalative (including, but not limited to, pulmonary, aerosol inhalation), nasal, sublingual, subcutaneous or intraarticular formulations, comprising the heterocyclic metalloprotease inhibiting compounds by standard methods known in medical practice, for the treatment of diseases or symptoms arising from or associated with metalloprotease, especially MMP-13, including prophylactic and therapeutic treatment. Although the most suitable route in any given case will depend on the nature and severity of the conditions being treated and on the nature of the active ingredient. The compounds from this invention are conveniently presented in unit dosage form and prepared by any of the methods well-known in the art of pharmacy.

The heterocyclic metalloprotease inhibiting compounds of the present invention may be used in combination with a disease modifying antirheumatic drug, a nonsteroidal anti-inflammatory drug, a COX-2 selective inhibitor, a COX-1 inhibitor, an immunosuppressive, a steroid, a biological response modifier, a viscosupplement, a pain reducing drug or other anti-inflammatory agents or therapeutics useful for the treatment of chemokines mediated diseases.

DETAILED DESCRIPTION OF THE INVENTION

One aspect of the invention relates to a compound having Formula (I):

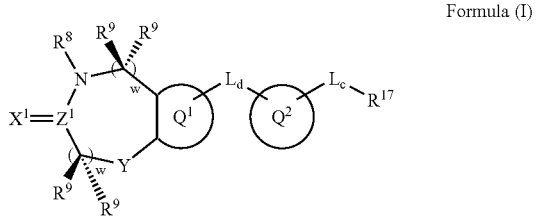

Formula (I)

wherein:

$R^4$ in each occurrence is independently selected from $R^{10}$, hydrogen, alkyl, cycloalkyl, heterocycloalkyl, aryl, heteroaryl, halo, haloalkyl, $CF_3$, $(C_0-C_6)$-alkyl-$COR^{10}$, $(C_0-C_6)$-alkyl-$OR^{10}$, $(C_0-C_6)$-alkyl-$NR^{10}R^{11}$, $(C_0-C_6)$-alkyl-$NO_2$, $(C_0-C_6)$-alkyl-CN, $(C_0-C_6)$-alkyl-$S(O)_yOR^{10}$, $(C_0-C_6)$-alkyl-$S(O)_yNR^{10}R^{11}$, $(C_0-C_6)$-alkyl-$NR^{10}CONR^{11}SO_2R^{30}$, $(C_0-C_6)$-alkyl-$S(O)_xR^{10}$, $(C_0-C_6)$-alkyl-$OC(O)R^{10}$, $(C_0-C_6)$-alkyl-$OC(O)NR^{10}R^{11}$, $(C_0-C_6)$-alkyl-$C(=NR^{10})NR^{10}R^{11}$, $(C_0-C_6)$-alkyl-$NR^{10}C(=NR^{11})NR^{10}R^{11}$, $(C_0-C_6)$-alkyl-$C(O)OR^{10}$, $(C_0-C_6)$-alkyl-$C(O)NR^{10}R^{11}$, $(C_0-C_6)$-alkyl-$C(O)NR^{10}SO_2R^{11}$, $(C_0-C_6)$-alkyl-$C(O)$—$NR^{11}$—CN, O—$(C_0-C_6)$-alkyl-$C(O)NR^{10}R^{11}$, $S(O)_x$—$(C_0-C_6)$-alkyl-$C(O)OR^{10}$, $S(O)_x$—$(C_0-C_6)$-alkyl-$C(O)NR^{10}R^{11}$, $(C_0-C_6)$-alkyl-$C(O)NR^{10}$—$(C_0-C_6)$-alkyl-$NR^{10}R^{11}$, $(C_0-C_6)$-alkyl-$NR^{10}$—$C(O)R^{10}$, $(C_0-C_6)$-alkyl-$NR^{10}$—$C(O)OR^{10}$, $(C_0-C_6)$-alkyl-$NR^{10}$—$C(O)$—$NR^{10}R^{11}$, $(C_0-C_6)$-alkyl-$NR^{10}$—$S(O)_yNR^{10}R^{11}$, $(C_0-C_6)$-alkyl-$NR^{10}$—$S(O)_yR^{10}$, O—$(C_0-C_6)$-alkyl-aryl and O—$(C_0-C_6)$-alkyl-heteroaryl, wherein each $R^4$ group is optionally substituted one or more times, or wherein each $R^4$ group is optionally substituted by one or more $R^{14}$ groups;

$R^8$ is selected from $R^{10}$ or optionally $R^8$ and $X^1$ when taken together with the nitrogen and $sp^2$-carbon atom to which they are attached complete a 5- to 8-membered unsaturated or partially unsaturated heterocycle optionally containing additional heteroatoms selected from O, $S(O)_x$, N or $NR^{50}$ and which is optionally substituted one or more times;

$R^9$ in each occurrence is independently selected from $R^{10}$, hydrogen, alkyl, cycloalkyl, heterocycloalkyl, aryl, heteroaryl, halo, $CHF_2$, $CF_3$, $OR^{10}$, $SR^{10}$, $COOR^{10}$, $CH(CH_3)CO_2H$, $(C_0-C_6)$-alkyl-$COR^{10}$, $(C_0-C_6)$-alkyl-$OR^{10}$, $(C_0-C_6)$-alkyl-$NR^{10}R^{11}$, $(C_0-C_6)$-alkyl-$NO_2$, $(C_0-C_6)$-alkyl-CN, $(C_0-C_6)$-alkyl-$S(O)_yOR^{10}$, $(C_0-C_6)$-alkyl-$P(O)_2OH$, $(C_0-C_6)$-alkyl-$S(O)_yNR^{10}R^{11}$, $(C_0-C_6)$-alkyl-$NR^{10}CONR^{11}SO_2R^{30}$, $(C_0-C_6)$-alkyl-$S(O)_xR^{10}$, $(C_0-C_6)$-alkyl-$OC(O)R^{10}$, $(C_0-C_6)$-alkyl-$OC(O)NR^{10}R^{11}$, $(C_0-C_6)$-alkyl-$C(=NR^{10})NR^{10}R^{11}$, $(C_0-C_6)$-alkyl-$NR^{10}C(=NR^{11})NR^{10}R^{11}$, $(C_0-C_6)$-alkyl-$NR^{10}C(=N-CN)NR^{10}R^{11}$, $(C_0-C_6)$-alkyl-$C(=N-CN)NR^{10}R^{11}$, $(C_0-C_6)$-alkyl-$NR^{10}C(=N-NO_2)NR^{10}R^{11}$, $(C_0-C_6)$-alkyl-$C(=N-NO_2)NR^{10}R^{11}$, $(C_0-C_6)$-alkyl-$C(O)OR^{10}$, $(C_0-C_6)$-alkyl-$C(O)NR^{10}R^{11}$, $(C_0-C_6)$-alkyl-$C(O)NR^{10}SO_2R^{11}$, $C(O)NR^{10}$—$(C_0-C_6)$-alkyl-heteroaryl, $C(O)NR^{10}$—$(C_0-C_6)$-alkyl-aryl, $S(O)_2NR^{10}$—$(C_0-C_6)$-alkyl-aryl, $S(O)_2NR^{10}$—$(C_0-C_6)$-alkyl-heteroaryl, $S(O)_2NR^{10}$-alkyl, $S(O)_2$—$(C_0-C_6)$-alkyl-aryl, $S(O)_2$—$(C_0-C_6)$-alkyl-heteroaryl, $(C_0-C_6)$-alkyl-$C(O)$—$NR^{11}$—CN, O—$(C_0-C_6)$-alkyl-$C(O)NR^{10}R^{11}$, $S(O)_x$—$(C_0-C_6)$-alkyl-$C(O)OR^{10}$, $S(O)_x$—$(C_0-C_6)$-alkyl-$C(O)NR^{10}R^{11}$, $(C_0-C_6)$-alkyl-$C(O)NR^{10}$—$(C_0-C_6)$-alkyl-$NR^{10}R^{11}$, $(C_0-C_6)$-alkyl-$NR^{10}$—$C(O)R^{10}$, $(C_0-C_6)$-alkyl-$NR^{10}$—$C(O)OR^{10}$, $(C_0-C_6)$-alkyl-$NR^{10}$—$C(O)$—$NR^{10}R^{11}$, $(C_0-C_6)$-alkyl-$NR^{10}$—$S(O)_yNR^{10}R^{11}$, $(C_0-C_6)$-alkyl-$NR^{10}$—$S(O)_yR^{10}$, O—$(C_0-C_6)$-alkyl-aryl and O—$(C_0-C_6)$-alkyl-heteroaryl, wherein each $R^9$ group is optionally one or more times substituted;

$R^{10}$ and $R^{11}$ in each occurrence are independently selected from hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted one or more times, or $R^{10}$ and $R^{11}$ when taken together with the nitrogen to which they are attached complete a 3- to 8-membered ring containing carbon atoms and optionally containing a heteroatom selected from O, $S(O)_x$, or $NR^{50}$ and which is optionally substituted one or more times;

$R^{14}$ is independently selected from hydrogen, alkyl, arylalkyl, cycloalkylalkyl, heteroarylalkyl, heterocyclylalkyl and halo, wherein alkyl, arylalkyl, cycloalkylalkyl, heteroarylalkyl and heterocyclylalkyl are optionally substituted one or more times;

$R^{17}$ is selected from $R^9$, alkenyl, alkynyl, bicycloalkyl, heterobicycloalkyl, spiroalkyl, spiroheteroalkyl, cycloalkyl fused aryl, heterocycloalkyl fused aryl, cycloalkyl fused heteroaryl, heterocycloalkyl fused heteroaryl or a bicyclic or tricyclic fused ring system, wherein at least one ring is partially saturated, and wherein each $R^{17}$ group is optionally substituted one or more times, or wherein each $R^{17}$ group is optionally substituted one or more $R^9$ groups;

$R^{30}$ is selected from alkyl and $(C_0-C_6)$-alkyl-aryl, wherein alkyl and aryl are optionally substituted;

$R^{50}$ in each occurrence is independently selected from hydrogen, alkyl, aryl, heteroaryl, $C(O)R^{80}$, $C(O)NR^{80}R^{81}$, $SO_2R^{80}$ and $SO_2NR^{80}R^{81}$, wherein alkyl, aryl, and heteroaryl are optionally substituted one or more times;

$R^{80}$ and $R^{81}$ in each occurrence are independently selected from hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{80}$ and $R^{81}$ when taken together with the nitrogen to which they are attached complete a 3- to 8-membered ring containing carbon atoms and optionally a heteroatom selected from O, $S(O)_x$, NH, and N(alkyl) and which is optionally substituted one or more times;

$L_c$ is selected from a single bond or an acyclic, straight or branched, saturated or unsaturated hydrocarbon chain having 1 to 10 carbon atoms, optionally containing 1 to 3 groups independently selected from —S—, —O—, NR¹⁰—, —NR¹⁰CO—, —CONR¹⁰—, —S(O)$_x$—, —SO$_2$NR¹⁰—, —NR¹⁰SO$_2$—, NR¹⁰SO$_2$NR¹⁰—, —NR¹⁰CONR¹⁰—, —OC(O)NR¹⁰—, —NR¹⁰C(O)O—, which replace single carbon atoms, which in case that more than two carbon atoms are replaced are not adjacent, and wherein the hydrocarbon chain is optionally substituted one or more times;

L$_d$ is selected from a single bond or a straight or branched, saturated or unsaturated hydrocarbon chain having 1 to 10 carbon atoms, optionally containing 1 to 3 groups independently selected from —O—, —NR¹⁰—, —S(O)$_x$—, —NR¹⁰C(X¹)—, —C(X¹)NR¹⁰—, —SO$_2$NR¹⁰—, —NR¹⁰SO$_2$—, —O—SO$_2$—, —SO$_2$—O—, —NR¹⁰SO$_2$NR¹⁰—, —NR¹⁰C(X¹)NR¹⁰—, —OC(X¹)NR¹⁰—, —NR¹⁰C(X¹)O—, —OC(X¹)—, —C(X¹)O—, -Q²-, —NR¹⁰-Q²-, -Q²-NR¹⁰—, —C(X¹)-Q²-, -Q²-C(X¹)—, —O-Q²-, —S(O)$_x$-Q²-, and -Q²-S(O)$_x$— which replace single carbon atoms, which in case that more than two carbon atoms are replaced are not adjacent, and wherein the hydrocarbon chain is optionally substituted one or more times;

Q¹ is a 4- to 8-membered ring selected from cycloalkyl, heterocycloalkyl, bicycloalkyl, heterobicycloalkyl or a 5- or 6-membered ring selected from aryl and heteroaryl, wherein cycloalkyl, heterocycloalkyl, bicycloalkyl, heterobicycloalkyl, aryl and heteroaryl are optionally substituted one or more times by R⁴ and optionally a substituent of Q¹ is linked with L$_d$ to complete a 3- to 8-membered ring containing carbon atoms and optionally heteroatoms selected from O, S(O)$_x$, —NH, and —N(alkyl) wherein this new ring is optionally substituted one or more times;

Q² is independently selected from an aromatic, partially aromatic or non-aromatic cyclic, bicyclic or multicyclic system containing 0 to 8 heteroatoms selected from N, O and S(O)$_x$, which is optionally substituted one or more times with R⁴ and wherein the cycles are optionally spiro fused and optionally a substituent of Q² is linked with L$_d$ to complete a 3- to 8-membered ring containing carbon atoms and optionally heteroatoms selected from O, S(O)$_x$, —NH, and —N(alkyl) wherein this new ring is optionally substituted one or more times;

X¹ is independently selected from S, NR¹⁰, NOR¹⁰, N—CN, NCOR¹⁰, N—NO$_2$, and N—SO$_2$R¹⁰;

Y is selected from O, S(O)$_x$, CR¹⁰R¹¹, and NR¹⁰;

Z¹ is independently selected from C, S, S=O, PR¹⁰ and P—OR¹⁰;

w is independently selected from 0 to 3;

x is independently selected from 0 to 2;

y is selected from 1 and 2; and

N-oxides, pharmaceutically acceptable salts, prodrugs, formulations, polymorphs, racemic mixtures and stereoisomers thereof.

In one embodiment, in conjunction with any above or below embodiments, Q² selected from:

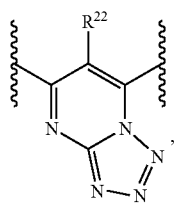 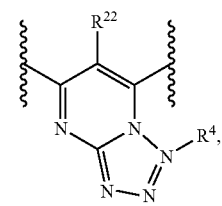

-continued

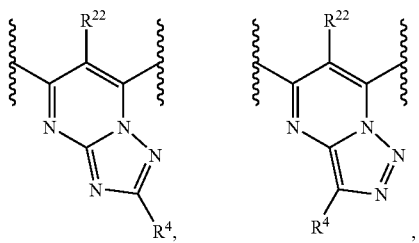

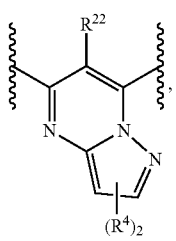 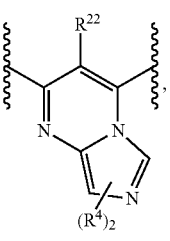

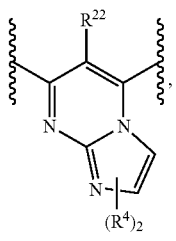 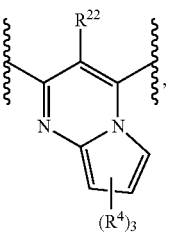

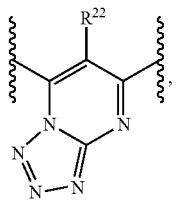 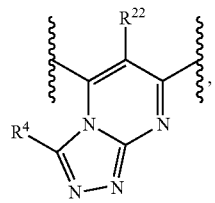

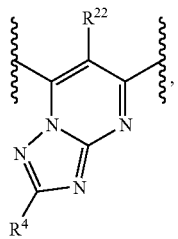 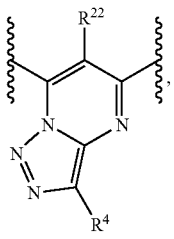

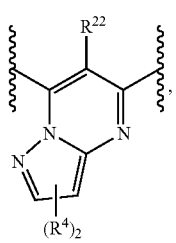 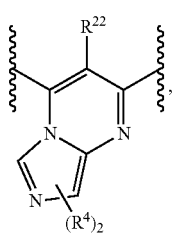

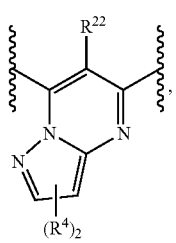 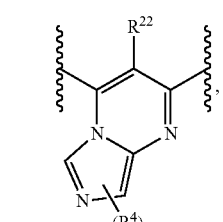

-continued

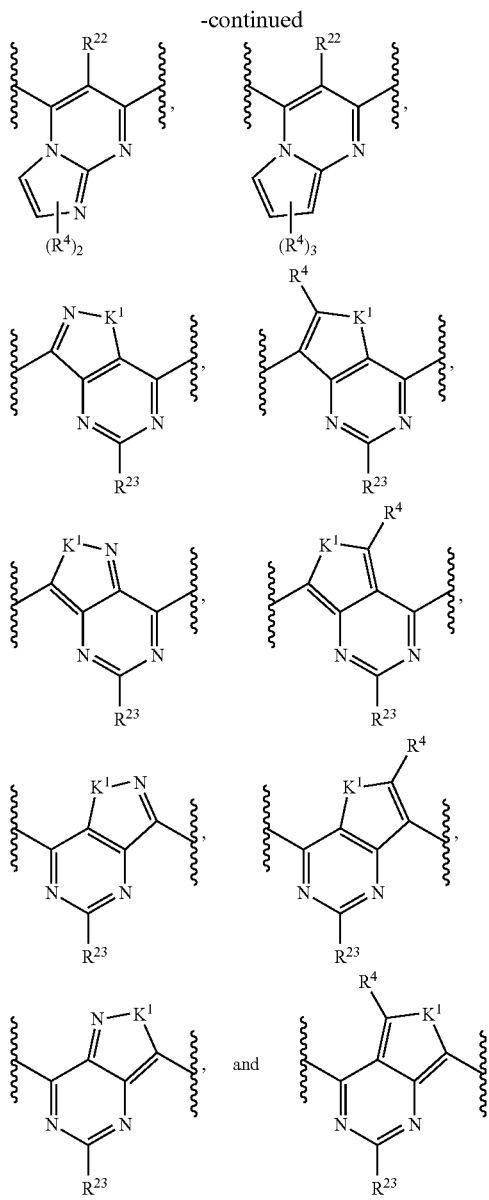

wherein:

R²² is selected from hydrogen, hydroxy, halo, alkyl, cycloalkyl, alkoxy, alkenyl, alkynyl, NO₂, NR¹⁰R¹¹, CN, SR¹⁰, SSR¹⁰, PO₃R¹⁰, NR¹⁰NR¹⁰R¹¹, NR¹⁰N=CR¹⁰R¹¹, NR¹⁰SO₂R¹¹, C(O)OR¹⁰, C(O)NR¹⁰R¹¹, SO₂R¹⁰, SO₂NR¹⁰R¹¹, and fluoroalkyl, wherein alkyl, cycloalkyl, alkoxy, alkenyl, alkynyl, and fluoroalkyl are optionally substituted one or more times;

R¹³ is selected from hydrogen, hydroxy, halo, alkyl, cycloalkyl, alkoxy, alkenyl, alkynyl, NO₂, NR¹⁰R¹¹, CN, SR¹⁰, SSR¹⁰, PO₃R¹⁰, NR¹⁰NR¹⁰R¹¹, NR¹⁰N=CR¹⁰R¹¹, NR¹⁰SO₂R¹¹, C(O)OR¹⁰, and fluoroalkyl, wherein alkyl, cycloalkyl, alkoxy, alkenyl, alkynyl, and fluoroalkyl are optionally substituted one or more times;

R⁵¹ is independently selected from hydrogen, alkyl, aryl, heteroaryl, arylalkyl, cycloalkylalkyl, heteroarylalkyl and haloalkyl, wherein alkyl, aryl, heteroaryl, arylalkyl, cycloalkylalkyl, heteroarylalkyl and haloalkyl are optionally substituted one or more times; and K¹ is O, S(O)ₓ, or NR⁵¹.

In one embodiment, in conjunction with any above or below embodiments, the compound is:

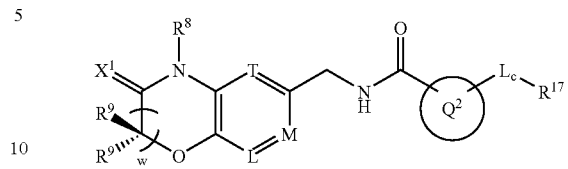

wherein:

L, M and T are independently selected from CR⁹ and N.

In one embodiment, in conjunction with any above or below embodiments, the compound is selected from:

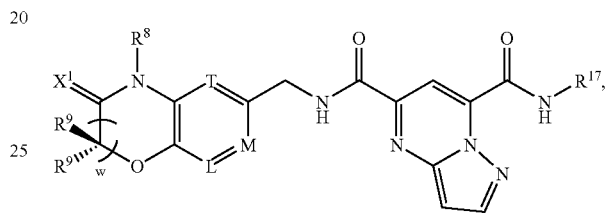

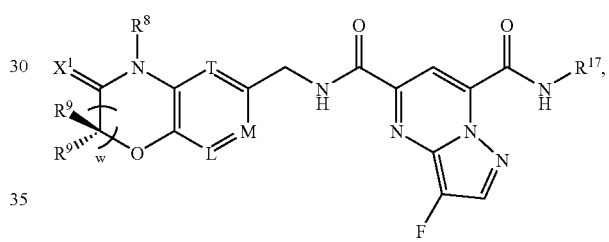

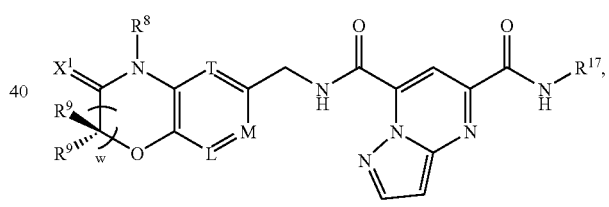

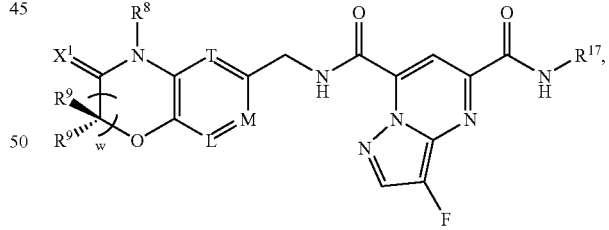

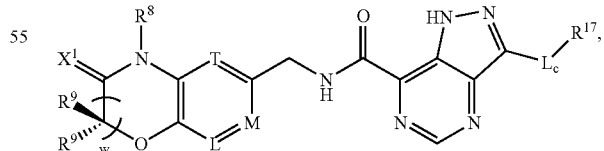

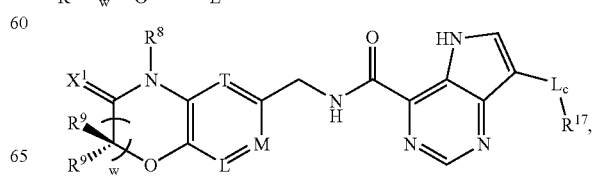

-continued

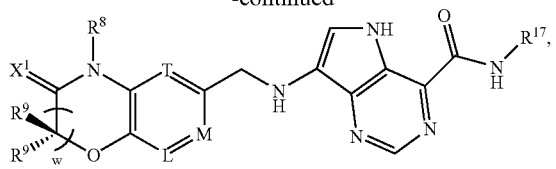

and

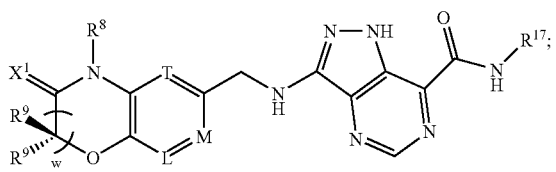

wherein:

$L_c$ is selected from —SO$_2$NR$^{10}$—, —S(O)$_x$—, S(O)$_2$O—, —C(O)O—, —C(O)NR$^{10}$—, —NR$^{10}$—, —NR$^{10}$SO$_2$—, —OC(O)—, —OC(O)NR$^{10}$, NR$^{10}$C(O)—, —NR$^{10}$CO$_2$—, —NR$^{10}$C(O)NR$^{10}$—, —NR$^{10}$C(=NR$^{10}$)—, and —O—.

In one embodiment, in conjunction with any above or below embodiments, the compound of claim 4 selected from:

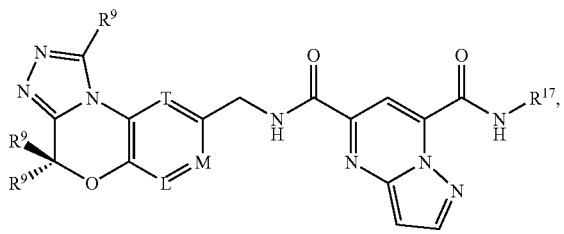

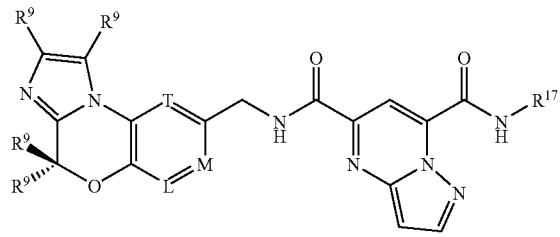

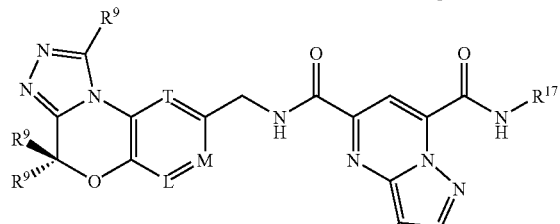

and

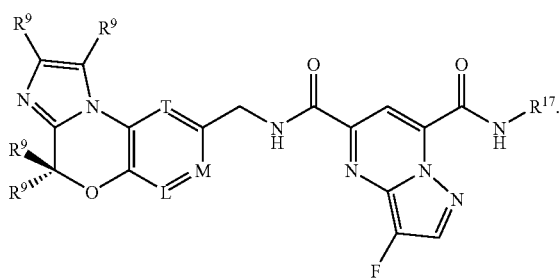

In one embodiment, in conjunction with any above or below embodiments, R$^{17}$ is selected from:

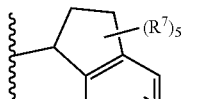 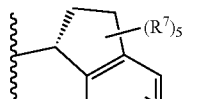

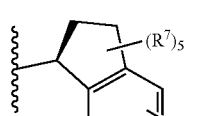 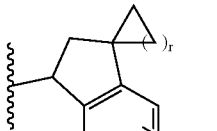

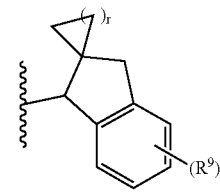 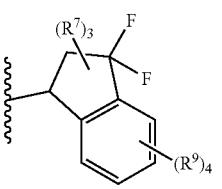

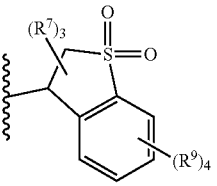 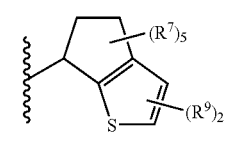

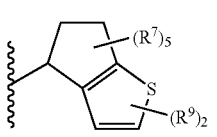 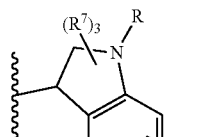

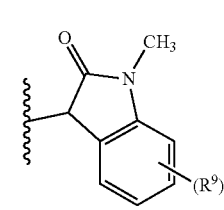 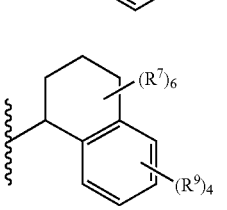

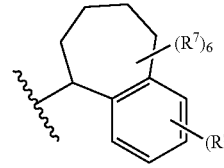

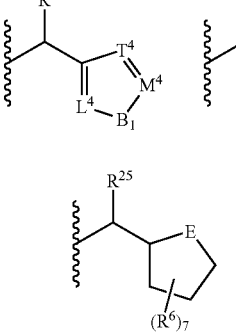 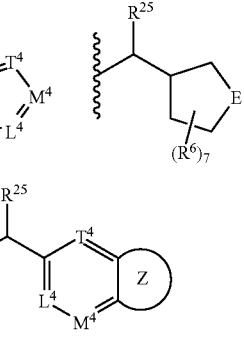

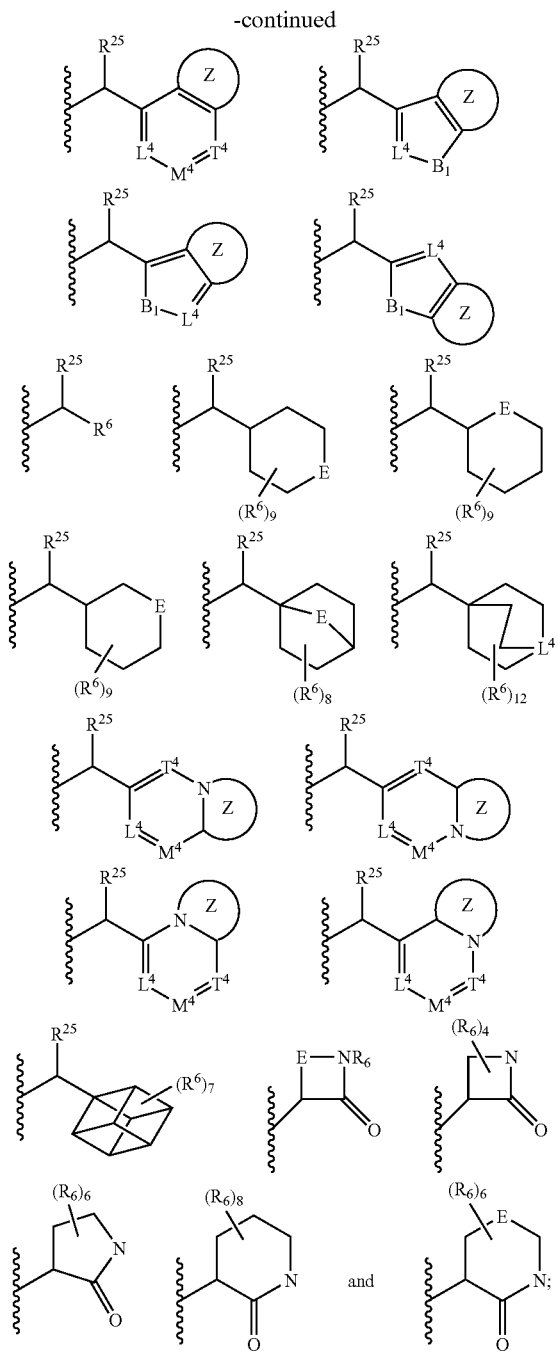

-continued wherein:

R is selected from C(O)NR$^{10}$R$^{11}$, COR$^{10}$, SO$_2$NR$^{10}$R$^{11}$, SO$_2$R$^{10}$, CONHCH$_3$ and CON(CH$_3$)$_2$, wherein C(O)NR$^{10}$R$^{11}$, COR$^{10}$, SO$_2$NR$^{10}$R$^{11}$, SO$_2$R$^{10}$, CONHCH$_3$ and CON(CH$_3$)$_2$ are optionally substituted one or more times;

R$^5$ in each occurrence is independently selected from hydrogen, alkyl, C(O)NR$^{10}$R$^{11}$, aryl, arylalkyl, SO$_2$NR$^{10}$R$^{11}$ and C(O)OR$^{10}$, wherein alkyl, aryl and arylalkyl are optionally substituted one or more times;

R$^6$ is independently selected from R$^9$, alkenyl, alkynyl, cycloalkyl, heterocycloalkyl, bicycloalkyl, heterobicycloalkyl, spiroalkyl, spiroheteroalkyl, aryl, heteroaryl, C(O)OR$^{10}$, CH(CH$_3$)CO$_2$H, (C$_0$-C$_6$)-alkyl-COR$^{10}$, (C$_0$-C$_6$)-alkyl-OR$^{10}$, (C$_0$-C$_6$)-alkyl-NR$^{10}$R$^{11}$, (C$_0$-C$_6$)-alkyl-NO$_2$, (C$_0$-C$_6$)-alkyl-CN, (C$_0$-C$_6$)-alkyl-S(O)$_y$OR$^{10}$, (C$_0$-C$_6$)-alkyl-P(O)$_2$OH, (C$_0$-C$_6$)-alkyl-S(O)$_y$NR$^{10}$R$^{11}$, (C$_0$-C$_6$)-alkyl-NR$^{10}$CONR$^{11}$SO$_2$R$^{30}$, (C$_0$-C$_6$)-alkyl-S(O)$_x$R$^{10}$, (C$_0$-C$_6$)-alkyl-OC(O)R$^{10}$, (C$_0$-C$_6$)-alkyl-OC(O)NR$^{10}$R$^{11}$, (C$_0$-C$_6$)-alkyl-C(=NR$^{10}$)NR$^{10}$R$^{11}$, (C$_0$-C$_6$)-alkyl-NR$^{10}$C(=NR$^{11}$)NR$^{10}$R$^{11}$, (C$_0$-C$_6$)-alkyl-NR$^{10}$C(=N—CN)NR$^{10}$R$^{11}$, (C$_0$-C$_6$)-alkyl-C(=N—CN)NR$^{10}$R$^{11}$, (C$_0$-C$_6$)-alkyl-NR$^{10}$C(=N—NO$_2$)NR$^{10}$R$^{11}$, (C$_0$-C$_6$)-alkyl-C(=N—NO$_2$)NR$^{10}$R$^{11}$, (C$_0$-C$_6$)-alkyl-C(O)OR$^{10}$, (C$_0$-C$_6$)-alkyl-C(O)NR$^{10}$R$^{11}$, (C$_0$-C$_6$)-alkyl-C(O)NR$^{10}$SO$_2$R$^{11}$, C(O)NR$^{10}$—(C$_0$-C$_6$)-alkyl-heteroaryl, C(O)NR$^{10}$—(C$_0$-C$_6$)-alkyl-aryl, S(O)$_2$NR$^{10}$—(C$_0$-C$_6$)-alkyl-aryl, S(O)$_2$NR$^{10}$—(C$_0$-C$_6$)-alkyl-heteroaryl, S(O)$_2$NR$^{10}$-alkyl, S(O)$_2$—(C$_0$-C$_6$)-alkyl-aryl, S(O)$_2$—(C$_0$-C$_6$)-alkyl-heteroaryl, (C$_0$-C$_6$)-alkyl-C(O)—NR$^{11}$—CN, O—(C$_0$-C$_6$)-alkyl-C(O)NR$^{10}$R$^{11}$, S(O)$_x$—(C$_0$-C$_6$)-alkyl-C(O)OR$^{10}$, S(O)$_x$—(C$_0$-C$_6$)-alkyl-C(O)NR$^{10}$R$^{11}$, (C$_0$-C$_6$)-alkyl-C(O)NR$^{10}$—(C$_0$-C$_6$)-alkyl-NR$^{10}$R$^{11}$, (C$_0$-C$_6$)-alkyl-NR$^{10}$—C(O)R$^{10}$, (C$_0$-C$_6$)-alkyl-NR$^{10}$—C(O)OR$^{10}$, (C$_0$-C$_6$)-alkyl-NR$^{10}$—C(O)—NR$^{10}$R$^{11}$, (C$_0$-C$_6$)-alkyl-NR$^{10}$—S(O)$_y$NR$^{10}$R$^{11}$, (C$_0$-C$_6$)-alkyl-NR$^{10}$—S(O)$_y$R$^{11}$, O—(C$_0$-C$_6$)-alkyl-aryl and O—(C$_0$-C$_6$)-alkyl-heteroaryl, wherein each R$^6$ group is optionally substituted one or more times, or wherein each R$^6$ group is optionally substituted by one or more R$^{14}$ groups;

R$^7$ is independently selected from hydrogen, alkyl, cycloalkyl, halo, R$^4$ and NR$^{10}$R$^{11}$, wherein alkyl and cycloalkyl are optionally substituted one or more times, or optionally two R$^7$ groups together at the same carbon atom form =O, =S or =NR$^{10}$;

R$^{15}$ is independently selected from hydrogen, alkyl, cycloalkyl, C(O)R$^{10}$, C(O)NR$^{10}$R$^{11}$ and haloalkyl, wherein alkyl, cycloalkyl, and haloalkyl are optionally substituted one or more times;

B$_1$ is selected from NR$^{10}$, O and S(O)$_x$;

D$^4$, G$^4$, L$^4$, M$^4$, and T$^4$, are independently selected from CR$^6$ and N;

E is independently selected from a bond, CR$^{10}$R$^{11}$, O, NR$^5$, S, S=O, S(=O)$_2$, C(=O), N(R$^{10}$)(C=O), (C=O)N(R$^{10}$), N(R$^{10}$)S(=O)$_2$, S(=O)$_2$N(R$^{10}$), C=N—OR$^{11}$, —C(R$^{10}$R$^{11}$)C(R$^{10}$R$^{11}$)—, —CH$_2$—W$^1$— and

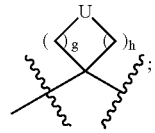

U is independently selected from C(R$^5$R$^{10}$), NR$^5$, O, S, S=O and S(=O)$_2$;

W$^1$ is independently selected from O, NR$^5$, S, S=O, S(=O)$_2$, N(R$^{10}$)(C=O), N(R$^{10}$)S(=O)$_2$ and S(=O)$_2$N(R$^{10}$);

Z is a 4- to 8-membered ring consisting of cycloalkyl, heterocycloalkyl or a 5- or 6-membered ring selected from aryl and heteroaryl, wherein cycloalkyl, heterocycloalkyl, aryl and heteroaryl are optionally substituted one or more times;

g and h are independently selected from 0-2; and r is selected from 1-4.

In one embodiment, in conjunction with any above or below embodiments, R$^{17}$ is selected from:

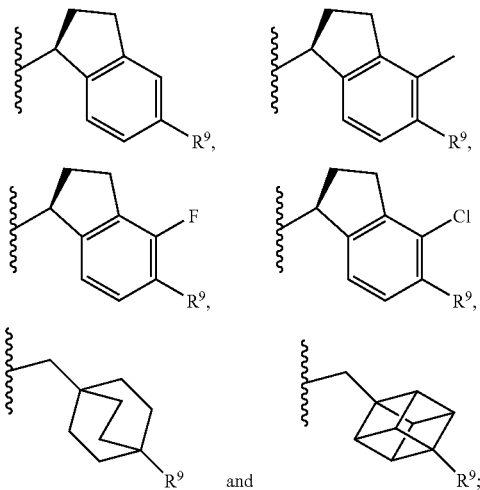

and wherein $R^9$ is selected from hydrogen, fluoro, halo, CN, alkyl, $CO_2H$,

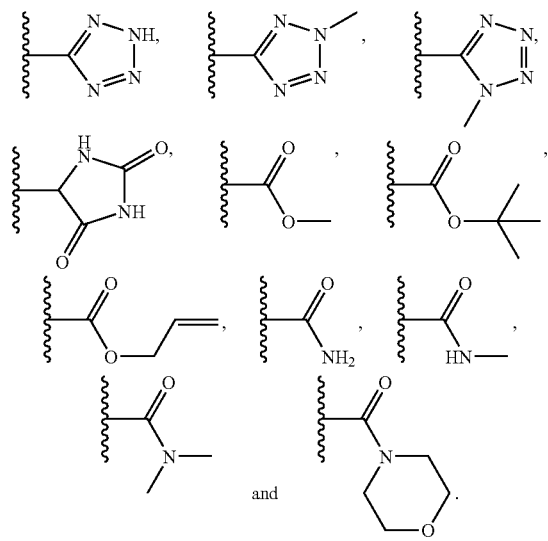

In one embodiment, in conjunction with any above or below embodiments, the compound is selected from:

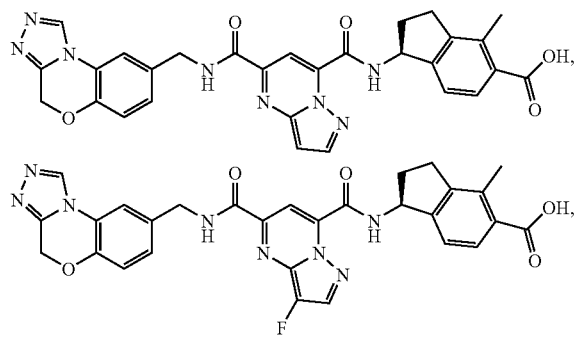

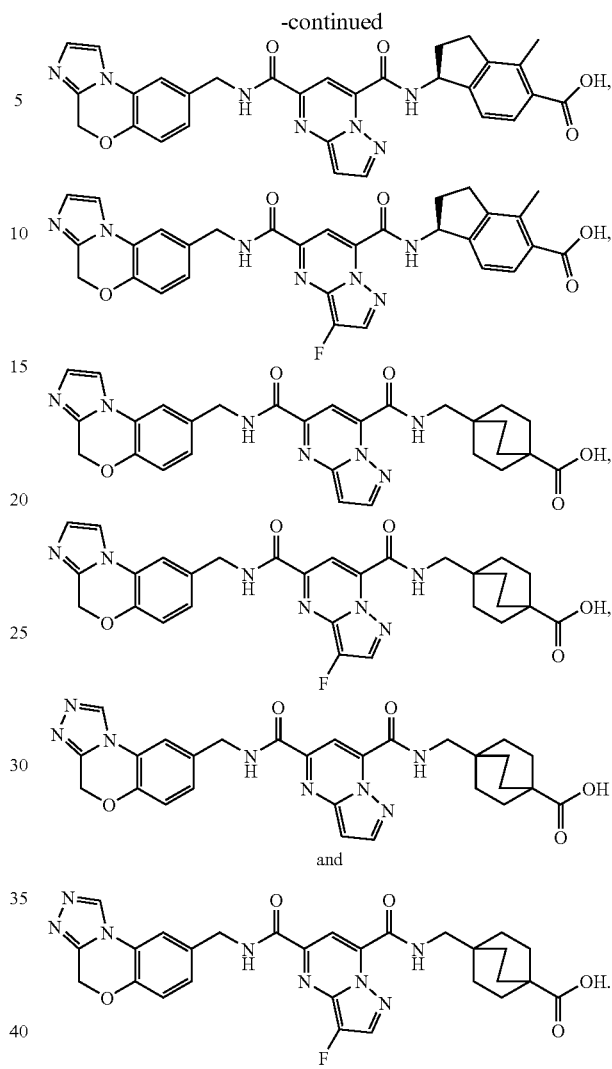

In one embodiment, in conjunction with any above or below embodiments, $R^4$ is substituted 0, 1 or 2 times.

In one embodiment, in conjunction with any above or below embodiments, $R^4$ is substituted by 0, 1 or 2 $R^{14}$ groups.

In one embodiment, in conjunction with any above or below embodiments, $R^6$ group is substituted 0, 1 or 2 times.

In one embodiment, in conjunction with any above or below embodiments, $R^6$ group is substituted by 0, 1 or 2 $R^{14}$ groups;

In one embodiment, in conjunction with any above or below embodiments, $R^7$ is independently selected from hydrogen, alkyl, cycloalkyl, halo, $R^4$ and $NR^{10}R^{11}$, wherein alkyl and cycloalkyl are optionally substituted one or more times, or optionally two $R^7$ groups together at the same carbon atom form =O, =S or $=NR^{10}$;

In one embodiment, in conjunction with any above or below embodiments, $R^8$ is $R^{10}$.

In one embodiment, in conjunction with any above or below embodiments, $R^8$ and $X^1$ when taken together with the nitrogen and sp²-carbon atom to which they are attached complete a 5- to 8-membered unsaturated or partially unsaturated heterocycle optionally containing additional heteroatoms selected from O, $S(O)_x$, N or $NR^{50}$ and which is substituted 0, 1 or 2 times.

In one embodiment, in conjunction with any above or below embodiments, one $R^9$ is selected from $R^{10}$, alkyl, cycloalkyl, heterocycloalkyl, aryl, heteroaryl, halo, $CHF_2$, $CF_3$, $OR^{10}$, $SR^{10}$, $COOR^{10}$, $CH(CH_3)CO_2H$, $(C_0\text{-}C_6)$-alkyl-$COR^{10}$, $(C_0\text{-}C_6)$-alkyl-$OR^{10}$, $(C_0\text{-}C_6)$-alkyl-$NR^{10}R^{11}$, $(C_0\text{-}C_6)$-alkyl-$NO_2$, $(C_0\text{-}C_6)$-alkyl-$CN$, $(C_0\text{-}C_6)$-alkyl-$S(O)_y\text{-}OR^{10}$, $(C_0\text{-}C_6)$-alkyl-$P(O)_2OH$, $(C_0\text{-}C_6)$-alkyl-$S(O)_y\text{-}NR^{10}R^{11}$, $(C_0\text{-}C_6)$-alkyl-$NR^{10}CONR^{11}SO_2R^{30}$, $(C_0\text{-}C_6)$-alkyl-$S(O)_xR^{10}$, $(C_0\text{-}C_6)$-alkyl-$OC(O)R^{10}$, $(C_0\text{-}C_6)$-alkyl-$OC(O)NR^{10}R^{11}$, $(C_0\text{-}C_6)$-alkyl-$C(=NR^{10})NR^{10}R^{11}$, $(C_0\text{-}C_6)$-alkyl-$NR^{10}C(=NR^{11})NR^{10}R^{11}$, $(C_0\text{-}C_6)$-alkyl-$NR^{10}C(=N\text{—}CN)NR^{10}R^{11}$, $(C_0\text{-}C_6)$-alkyl-$C(=N\text{—}CN)NR^{10}R^{11}$, $(C_0\text{-}C_6)$-alkyl-$NR^{10}C(=N\text{—}NO_2)NR^{10}R^{11}$, $(C_0\text{-}C_6)$-alkyl-$C(=N\text{—}NO_2)NR^{10}R^{11}$, $(C_0\text{-}C_6)$-alkyl-$C(O)OR^{10}$, $(C_0\text{-}C_6)$-alkyl-$C(O)NR^{10}R^{11}$, $(C_0\text{-}C_6)$-alkyl-$C(O)NR^{10}SO_2R^{11}$, $C(O)NR^{10}$—$(C_0\text{-}C_6)$-alkyl-heteroaryl, $C(O)NR^{10}$—$(C_0\text{-}C_6)$-alkyl-aryl, $S(O)_2NR^{10}$—$(C_0\text{-}C_6)$-alkyl-aryl, $S(O)_2NR^{10}$—$(C_0\text{-}C_6)$-alkyl-heteroaryl, $S(O)_2NR^{10}$-alkyl, $S(O)_2$—$(C_0\text{-}C_6)$-alkyl-aryl, $S(O)_2$—$(C_0\text{-}C_6)$-alkyl-heteroaryl, $(C_0\text{-}C_6)$-alkyl-$C(O)$—$NR^{11}$—$CN$, $O$—$(C_0\text{-}C_6)$-alkyl-$C(O)NR^{10}R^{11}$, $S(O)_x$—$(C_0\text{-}C_6)$-alkyl-$C(O)OR^{10}$, $S(O)_x$-$(C_0\text{-}C_6)$-alkyl-$C(O)NR^{10}R^{11}$, $(C_0\text{-}C_6)$-alkyl-$C(O)NR^{10}$—$(C_0\text{-}C_6)$-alkyl-$NR^{10}R^{11}$, $(C_0\text{-}C_6)$-alkyl-$NR^{10}$—$C(O)R^{10}$, $(C_0\text{-}C_6)$-alkyl-$NR^{10}$—$C(O)OR^{10}$, $(C_0\text{-}C_6)$-alkyl-$NR^{10}$—$C(O)$—$NR^{10}R^{11}$, $(C_0\text{-}C_6)$-alkyl-$NR^{10}$—$S(O)_yNR^{10}R^{11}$, $(C_0\text{-}C_6)$-alkyl-$NR^{10}$—$S(O)_yR^{11}$, $O$—$(C_0\text{-}C_6)$-alkyl-aryl and $O$—$(C_0\text{-}C_6)$-alkyl-heteroaryl, wherein each $R^9$ group is substituted 0, 1 or 2 times; and the remaining $R^9$ groups are hydrogen.

In one embodiment, in conjunction with any above or below embodiments, $R^9$ is H.

In one embodiment, in conjunction with any above or below embodiments, $R^{17}$ is selected from $R^9$, alkenyl, alkynyl, bicycloalkyl, heterobicycloalkyl, spiroalkyl, spiroheteroalkyl, cycloalkyl fused aryl, heterocycloalkyl fused aryl, cycloalkyl fused heteroaryl, heterocycloalkyl fused heteroaryl or a bicyclic or tricyclic fused ring system, wherein at least one ring is partially saturated, and wherein each $R^{17}$ group is substituted 0, 1 or 2 times and 0 or 1 $R^9$ groups.

In one embodiment, in conjunction with any above or below embodiments, $R^{30}$ is selected from alkyl and $(C_0\text{-}C_6)$-alkyl-aryl, wherein alkyl and aryl are optionally substituted 0, 1 or 2 times.

In one embodiment, in conjunction with any above or below embodiments, one $R^9$ is $sR^{50}$ in each occurrence is independently selected from hydrogen, alkyl, aryl, heteroaryl, $C(O)R^{80}$, $C(O)NR^{80}R^{81}$, $SO_2R^{80}$ and $SO_2NR^{80}R^{81}$, wherein alkyl, aryl, and heteroaryl are substituted 0, 1 or 2 times.

In one embodiment, in conjunction with any above or below embodiments, $R^{80}$ and $R^{81}$ in each occurrence are independently selected from hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted 0, 1 or 2 times, or $R^{80}$ and $R^{81}$ when taken together with the nitrogen to which they are attached complete a 3- to 8-membered ring containing carbon atoms and optionally a heteroatom selected from O, $S(O)_x$, NH, and N(alkyl) and which is optionally substituted 0, 1 or 2 times.

In one embodiment, in conjunction with any above or below embodiments, $L_c$ is selected from a single bond or an acyclic, straight or branched, saturated or unsaturated hydrocarbon chain having 1 to 10 carbon atoms, optionally containing 1 to 3 groups independently selected from —S—, —O—, $NR^{10}$—, —$NR^{10}CO$—, —$CONR^{10}$—, —$S(O)_x$—, —$SO_2NR^{10}$—, —$NR^{10}SO_2$—, $NR^{10}SO_2NR^0$—, —$NR^{10}CONR^{10}$—, —$OC(O)NR^{10}$—, —$NR^{10}C(O)O$—, which replace single carbon atoms, which in case that more than two carbon atoms are replaced are not adjacent, and wherein the hydrocarbon chain is optionally substituted one or more times;

In one embodiment, in conjunction with any above or below embodiments, $L_c$ is absent.

In one embodiment, in conjunction with any above or below embodiments, $L_c$ is selected from —CONH— and —NHCO—.

In one embodiment, in conjunction with any above or below embodiments, $L_d$ is selected from a single bond or a straight or branched, saturated or unsaturated hydrocarbon chain having 1 to 10 carbon atoms, optionally containing 1, 2 or 3 groups independently selected from —O—, —$NR^{10}$—, —$S(O)_x$—, —$NR^{10}C(X^1)$—, —$C(X^1)NR^{10}$—, —$SO_2NR^{10}$—, —$NR^{10}SO_2$—, —O—$SO_2$—, —$SO_2$—O—, —$NR^{10}SO_2NR^{10}$—, —$NR^{10}C(X^1)NR^{10}$—, —$OC(X^1)NR^{10}$—, —$NR^{10}C(X^1)O$—, —$OC(X^1)$—, —$C(X^1)O$—, -$Q^2$-, —$NR^{10}$-$Q^2$-, -$Q^2$-$NR^{10}$—, —$C(X^1)$-$Q^2$-, -$Q^2$-$C(X^1)$—, —O-$Q^2$-, —$S(O)_x$-$Q^2$-, and -$Q^2$-$S(O)X$— which replace single carbon atoms, which in case that more than two carbon atoms are replaced are not adjacent, and wherein the hydrocarbon chain is substituted 0, 1, 2 or 3 times;

In one embodiment, in conjunction with any above or below embodiments, $L_d$ is selected from —$CH_2NHCO$— and —$CH_2CONH$—.

In one embodiment, in conjunction with any above or below embodiments, $L_d$ is —$CH_2NHCO$—.

In one embodiment, in conjunction with any above or below embodiments, $Q^1$ is a 4-, 5-, 6-, 7- or 8-membered ring selected from cycloalkyl, heterocycloalkyl, bicycloalkyl, heterobicycloalkyl or a 5- or 6-membered ring selected from aryl and heteroaryl, wherein cycloalkyl, heterocycloalkyl, bicycloalkyl, heterobicycloalkyl, aryl and heteroaryl are substituted by 0, 1 or 2 $R^4$ groups and optionally a substituent of $Q^1$ is linked with $L_d$ to complete a 3- to 8-membered ring containing carbon atoms and optionally heteroatoms selected from O, $S(O)_x$, —NH, and —N(alkyl) wherein this new ring is optionally substituted one or more times.

In one embodiment, in conjunction with any above or below embodiments, $Q^1$ is phenyl.

In one embodiment, in conjunction with any above or below embodiments, $Q^1$ is pyridyl.

In one embodiment, in conjunction with any above or below embodiments, $Q^2$ is [fill in];

In one embodiment, in conjunction with any above or below embodiments, $X^1$ is O.

In one embodiment, in conjunction with any above or below embodiments, Y is O.

In one embodiment, in conjunction with any above or below embodiments, $Z^1$ is independently selected from C, S, S=O, $PR^{10}$ and P—$OR^{10}$.

Another aspect of the invention relates to a method of inhibiting a metalloprotease enzyme, comprising administering a compound selected from any of the above or below embodiments.

In another embodiment, in conjunction with any above or below embodiments, the metalloprotease is selected from MMP-3, MMP-8, and MMP-13.

In another embodiment, in conjunction with any above or below embodiments, the metalloprotease is MMP-13.

Another aspect of the invention relates to a method of treating a metalloprotease mediated disease, comprising administering to a subject in need of such treatment an effective amount of a compound selected from any of the above or below embodiments.

In another embodiment, in conjunction with any above or below embodiments, the disease is rheumatoid arthritis.

In another embodiment, in conjunction with any above or below embodiments, the disease is osteoarthritis.

In another embodiment, in conjunction with any above or below embodiments, the disease is inflammation.

In another embodiment, in conjunction with any above or below embodiments, the disease is atherosclerosis.

In another embodiment, in conjunction with any above or below embodiments, the disease is multiple sclerosis.

In another embodiment, in conjunction with any above or below embodiments, the disease is selected from: rheumatoid arthritis, osteoarthritis, abdominal aortic aneurysm, cancer (e.g. but not limited to melanoma, gastric carcinoma or non-small cell lung carcinoma), inflammation, atherosclerosis, chronic obstructive pulmonary disease, ocular diseases (e.g. but not limited to ocular inflammation, glaucoma, retinopathy of prematurity, macular degeneration with the wet type preferred and corneal neovascularization), neurologic diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimers disease, arterial plaque formation, oncology, periodontal, viral infection, stroke, atherosclerosis, cardiovascular disease, reperfusion injury, trauma, chemical exposure or oxidative damage to tissues, wound healing, hemorrhoid, skin beautifying, pain, inflammatory pain, bone pain and joint pain, acne, acute alcoholic hepatitis, acute inflammation, acute pancreatitis, acute respiratory distress syndrome, adult respiratory disease, airflow obstruction, airway hyperresponsiveness, alcoholic liver disease, allograft rejections, angiogenesis, angiogenic ocular disease, arthritis, asthma, atopic dermatitis, bronchiectasis, bronchiolitis, bronchiolitis obliterans, burn therapy, cardiac and renal reperfusion injury, celiac disease, cerebral and cardiac ischemia, CNS tumors, CNS vasculitis, colds, contusions, cor pulmonae, cough, Crohn's disease, chronic bronchitis, chronic inflammation, chronic pancreatitis, chronic sinusitis, crystal induced arthritis, cystic fibrosis, delayed type hypersensitivity reaction, duodenal ulcers, dyspnea, early transplantation rejection, emphysema, encephalitis, endotoxic shock, esophagitis, gastric ulcers, gingivitis, glomerulonephritis, glossitis, gout, graft vs. host reaction, gram negative sepsis, granulocytic ehrlichiosis, hepatitis viruses, herpes, herpes viruses, HIV, hypercapnea, hyperinflation, hyperoxia-induced inflammation, hypoxia, hypersensitivity, hypoxemia, inflammatory bowel disease, interstitial pneumonitis, ischemia reperfusion injury, kaposi's sarcoma associated virus, lupus, malaria, meningitis, multi-organ dysfunction, necrotizing enterocolitis, osteoporosis, chronic periodontitis, periodontitis, peritonitis associated with continuos ambulatory peritoneal dialysis (CAPD), pre-term labor, polymyositis, post surgical trauma, pruritis, psoriasis, psoriatic arthritis, pulmatory fibrosis, pulmatory hypertension, renal reperfusion injury, respiratory viruses, restinosis, right ventricular hypertrophy, sarcoidosis, septic shock, small airway disease, sprains, strains, subarachnoid hemorrhage, surgical lung volume reduction, thrombosis, toxic shock syndrome, transplant reperfusion injury, traumatic brain injury, ulcerative colitis, vasculitis, ventilation-perfusion mismatching, and wheeze.

Another aspect of the invention relates to a pharmaceutical composition comprising:

A) an effective amount of a compound according to any of the above or below embodiments;

B) a pharmaceutically acceptable carrier; and

C) a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; (h) a viscosupplement; (i) a pain reducing drug; and (j) a small molecule inhibitor of pro-inflammatory cytokine production.

Another aspect of the invention relates to the use of a compound according to any of the above or below embodiments in the manufacture of a medicament for treating a metalloprotease mediated disease.

Another aspect of the invention relates to the use of a compound according to any of the above or below embodiments in conjunction with a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; (h) a viscosupplement; (i) a pain reducing drug; and (j) a small molecule inhibitor of pro-inflammatory cytokine production, in the manufacture of a medicament for treating a metalloprotease mediated disease.

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The terms "lower alk" or "lower alkyl" as used herein, denote such optionally substituted groups as described above for alkyl having 1 to 4 carbon atoms in the normal chain.

The term "alkoxy" denotes an alkyl group as described above bonded through an oxygen linkage (—O—).

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include, but are not limited to, one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butynyl, pentynyl, hexynyl, heptynyl, octynyl, nonynyl, decynyl, and the like. Exemplary substituents may include, but are not limited to, one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "cycloalkyl", as used herein alone or as part of another group, denotes optionally substituted, saturated cyclic hydrocarbon ring systems, desirably containing one ring with 3 to 9 carbons. Exemplary unsubstituted such groups include, but are not limited to, cyclopropyl, cyclobutyl, cyclopentyl, cyclohexyl, cycloheptyl, cyclooctyl, cyclodecyl, and cyclododecyl. Exemplary substituents include, but are not limited to, one or more alkyl groups as described above, or one or more groups described above as alkyl substituents.

The term "bicycloalkyl", as used herein alone or as part of another group, denotes optionally substituted, saturated cyclic bridged hydrocarbon ring systems, desirably containing 2 or 3 rings and 3 to 9 carbons per ring. Exemplary unsubstituted such groups include, but are not limited to, adamantyl, bicyclo[2.2.2]octane, bicyclo[2.2.1]heptane and cubane. Exemplary substituents include, but are not limited to, one or more alkyl groups as described above, or one or more groups described above as alkyl substituents.

The term "spiroalkyl", as used herein alone or as part of another group, denotes optionally substituted, saturated hydrocarbon ring systems, wherein two rings of 3 to 9 carbons per ring are bridged via one carbon atom. Exemplary unsubstituted such groups include, but are not limited to, spiro[3.5]nonane, spiro[4.5]decane or spiro[2.5]octane. Exemplary substituents include, but are not limited to, one or more alkyl groups as described above, or one or more groups described above as alkyl substituents.

The term "spiroheteroalkyl", as used herein alone or as part of another group, denotes optionally substituted, saturated hydrocarbon ring systems, wherein two rings of 3 to 9 carbons per ring are bridged via one carbon atom and at least one carbon atom is replaced by a heteroatom independently selected from N, O and S. The nitrogen and sulfur heteroatoms may optionally be oxidized. Exemplary unsubstituted such groups include, but are not limited to, 1,3-diaza-spiro[4.5]decane-2,4-dione. Exemplary substituents include, but are not limited to, one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

Further examples of heterocycles include, but not are not limited to, "heterobicycloalkyl" groups such as 7-oxa-bicyclo[2.2.1]heptane, 7-aza-bicyclo[2.2.1]heptane, and 1-aza-bicyclo[2.2.2]octane.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3, 6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo[2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more substituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, imidazolyl, indolyl, indolizinyl, isoxazolyl, isoquinolinyl, isothiazolyl, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2, 4-diazolyl, thiomorpholino, thiophenyl, thiopyranyl, triazolyl and triazolonyl.

The phrase "fused" means, that the group, mentioned before "fused" is connected via two adjacent atoms to the ring system mentioned after "fused" to form a bicyclic system. For example, "heterocycloalkyl fused aryl" includes, but is not limited to, 2,3-dihydro-benzo[1,4]dioxine, 4H-benzo[1,4] oxazin-3-one, 3H-Benzooxazol-2-one and 3,4-dihydro-2H-benzo [f][1,4]oxazepin-5-one.

The term "amino" denotes the radical —$NH_2$ wherein one or both of the hydrogen atoms may be replaced by an optionally substituted hydrocarbon group. Exemplary amino groups include, but are not limited to, n-butylamino, tert-butylamino, methylpropylamino and ethyldimethylamino.

The term "cycloalkylalkyl" denotes a cycloalkyl-alkyl group wherein a cycloalkyl as described above is bonded through an alkyl, as defined above. Cycloalkylalkyl groups may contain a lower alkyl moiety. Exemplary cycloalkylalkyl groups include, but are not limited to, cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

The term "arylalkyl" denotes an aryl group as described above bonded through an alkyl, as defined above.

The term "heteroarylalkyl" denotes a heteroaryl group as described above bonded through an alkyl, as defined above.

The term "heterocyclylalkyl," or "heterocycloalkylalkyl," denotes a heterocyclyl group as described above bonded through an alkyl, as defined above.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "aminoalkyl" denotes an amino group as defined above bonded through an alkyl, as defined above.

The phrase "bicyclic fused ring system wherein at least one ring is partially saturated" denotes an 8- to 13-membered fused bicyclic ring group in which at least one of the rings is non-aromatic. The ring group has carbon atoms and optionally 1-4 heteroatoms independently selected from N, O and S. The nitrogen and sulfur heteroatoms may optionally be oxidized. Illustrative examples include, but are not limited to, indanyl, tetrahydronaphthyl, tetrahydroquinolyl and benzocycloheptyl.

The phrase "tricyclic fused ring system wherein at least one ring is partially saturated" denotes a 9- to 18-membered fused tricyclic ring group in which at least one of the rings is non-aromatic. The ring group has carbon atoms and optionally 1-7 heteroatoms independently selected from N, O and S. The nitrogen and sulfur heteroatoms may optionally, be oxidized. Illustrative examples include, but are not limited to, fluorene, 10,11-dihydro-5H-dibenzo[a,d]cycloheptene and 2,2a,7,7a-tetrahydro-1H-cyclobuta[a]indene.

The phrase "cyclic" denotes to a saturated, partially unsaturated or unsaturated ring group with one ring. The ring group has carbon atoms and optionally 1-10 heteroatoms independently selected from N, O and S. The nitrogen and sulfur heteroatoms may optionally be oxidized. Illustrative examples include, but are not limited to, cyclobutane, cyclohexene, morpholine, tetrahydrofurane, benzene, thiophene, imidazole.

The phrase "biyclic" denotes to a saturated, partially unsaturated or unsaturated ring group with two ring. The ring group has carbon atoms and optionally 1-10 heteroatoms independently selected from N, O and S. The nitrogen and sulfur heteroatoms may optionally be oxidized. The rings may be annulated or otherwise connected, e.g. via a spiro connectivity. Illustrative examples include, but are not limited to, indane, tetrahydronaphthalin, tetrahydroquinoline, benzocycloheptane, and 1,3-diaza-spiro[4.5]decane-2,4-dione.

The phrase "multicyclic" denotes to a saturated, partially unsaturated or unsaturated ring group with at least three rings. The ring group has carbon atoms and optionally 1-10 heteroatoms independently selected from N, O and S. The nitrogen and sulfur heteroatoms may optionally be oxidized. The rings may be annulated or otherwise connected, e.g. via a spiro connectivity. Illustrative examples include, but are not limited to, fluorene, adamantyl, bicyclo[2.2.2]octane, bicyclo[2.2.1]heptane, cubane, 10,11-dihydro-5H-dibenzo[a,d]cycloheptene, 2,2a,7,7a-tetrahydro-1H-cyclobuta[a]indene, 5,6,7,8-tetrahydro-benzo[4,5]thieno[2,3-d]pyrimidine, 11-oxa-3,5-diaza-tricyclo[6.2.1.0$^{2,7}$]undeca-2(7),3,5-triene, 3,5-diaza-tricyclo[6.2.2.0$^{2,7}$]dodeca-2(7),3-dien-6-one.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Examples therefore may be, but are not limited to, sodium, potassium, choline, lysine, arginine or N-methyl-glucamine salts, and the like.

The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts are found in *Remington's Pharmaceutical Sciences,* 18th ed., Mack Publishing Company, Easton, Pa., 1990, p. 1445, the disclosure of which is hereby incorporated by reference.

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The phrase "pharmaceutically acceptable carrier" denotes media generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Non-limiting examples of a pharmaceutically acceptable carrier are hyaluronic acid and salts thereof, and microspheres (including, but not limited to poly(D,L)-lactide-co-glycolic acid copolymer (PLGA), poly(L-lactic acid) (PLA), poly(caprolactone (PCL) and bovine serum albumin (BSA)). Descriptions of suitable pharmaceutically acceptable carriers, and factors involved in their selection, are found in a variety of readily available sources, e.g., *Remington's Pharmaceutical Sciences,* 17th ed., Mack Publishing Company, Easton, Pa., 1985, the contents of which are incorporated herein by reference.

Pharmaceutically acceptable carriers particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

The compositions of the invention may also be formulated as suspensions including a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Carriers suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

Cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. The amount of solubility enhancer employed will depend on the amount of the compound of the present invention in the composition.

The term "formulation" denotes a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier.

The term "N-oxide" denotes compounds that can be obtained in a known manner by reacting a compound of the present invention including a nitrogen atom (such as in a pyridyl group) with hydrogen peroxide or a peracid, such as 3-chloroperoxy-benzoic acid, in an inert solvent, such as dichloromethane, at a temperature between about −10° C. to 80° C., desirably about 0° C.

The term "polymorph" denotes a form of a chemical compound in a particular crystalline arrangement. Certain polymorphs may exhibit enhanced thermodynamic stability and may be more suitable than other polymorphic forms for inclusion in pharmaceutical formulations.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures.

The term "racemic mixture" denotes a mixture that is about 50% of one enantiomer and about 50% of the corresponding enantiomer relative to all chiral centers in the molecule. Thus, the invention encompasses all enantiomerically-pure, enantiomerically-enriched, and racemic mixtures of compounds of Formula (I).

Enantiomeric and stereoisomeric mixtures of compounds of the invention can be resolved into their component enantiomers or stereoisomers by well-known methods. Examples include, but are not limited to, the formation of chiral salts and the use of chiral or high performance liquid chromatography "HPLC" and the formation and crystallization of chiral salts. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); Wilen, S. H., Tables of Resolving Agents and Optical Resolutions p. 268 (E. L. Eliel, Ed., Univ. of Notre Dame Press, Notre Dame, Ind., 1972); Stereochemistry of Organic Compounds, Ernest L. Eliel, Samuel H. Wilen and Lewis N. Manda (1994 John Wiley & Sons, Inc.), and Stereoselective Synthesis A Practical Approach, Mihaly Nogradi (1995 VCH Publishers, Inc., NY, N.Y.). Enantiomers and stereoisomers can also be obtained from stereomerically- or enantiomerically-pure intermediates, reagents, and catalysts by well-known asymmetric synthetic methods.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then two hydrogens on the atom are replaced. Furthermore two hydrogens on the atom can be replaced to form a thiocarbonyl (i.e., =S) or =N—NO$_2$, =N—CN, =N—H, =N—(C$_1$-C$_4$)alkyl, =N—OH, =N—O(C$_1$-C$_4$)alkyl, =N—CO(C$_1$-C$_4$)alkyl, and =N—SO$_2$(C$_1$-C$_4$)alkyl.

Unless moieties of a compound of the present invention are defined as being unsubstituted, the moieties of the compound may be substituted. In addition to any substituents provided above, the moieties of the compounds of the present invention may be optionally substituted with one or more groups independently selected from:

B(OH)$_2$;

B(O—(C$_1$-C)alkyl)$_2$;

C$_1$-C$_4$ alkyl;

C$_2$-C$_4$ alkenyl;

C$_2$-C$_4$ alkynyl;

CF$_3$;

halo;

OH;

O—(C$_1$-C$_4$ alkyl);

OCH$_2$F;

OCHF$_2$;

OCF$_3$;

ONO$_2$;

OC(O)—(C$_1$-C$_4$ alkyl);

OC(O)—(C$_1$-C$_4$ alkyl);

OC(O)NH—(C$_1$-C$_4$ alkyl);

OC(O)N(C$_1$-C$_4$ alkyl)$_2$;

OC(S)NH—(C$_1$-C$_4$ alkyl);

OC(S)N(C$_1$-C$_4$ alkyl)$_2$;

SH;

S—(C$_1$-C$_4$ alkyl);

S(O)—(C$_1$-C$_4$ alkyl);

S(O)$_2$—(C$_1$-C$_4$ alkyl);

SC(O)—(C$_1$-C$_4$ alkyl);

SC(O)O—(C$_1$-C$_4$ alkyl);

NH$_2$;

N(H)—(C$_1$-C$_4$ alkyl);

N(C$_1$-C$_4$ alkyl)$_2$;

N(H)C(O)—(C$_1$-C$_4$ alkyl);

N(CH$_3$)C(O)—(C$_1$-C$_4$ alkyl);

N(H)C(O)—CF$_3$;

N(CH$_3$)C(O)—CF$_3$;

N(H)C(S)—(C$_1$-C$_4$ alkyl);

N(CH$_3$)C(S)—(C$_1$-C$_4$ alkyl);

N(H)S(O)$_2$—(C$_1$-C$_4$ alkyl);

N(H)C(O)NH$_2$;

N(H)C(O)NH—(C$_1$-C$_4$ alkyl);

N(CH$_3$)C(O)NH—(C$_1$-C$_4$ alkyl);

N(H)C(O)N(C$_1$-C$_4$ alkyl)$_2$;

N(CH$_3$)C(O)N(C$_1$-C$_4$ alkyl)$_2$;

N(H)S(O)$_2$NH$_2$);

N(H)S(O)$_2$NH—(C$_1$-C$_4$ alkyl);

N(CH$_3$)S(O)$_2$NH—(C$_1$-C$_4$ alkyl);

N(H)S(O)$_2$N(C$_1$-C$_4$ alkyl)$_2$;

N(CH$_3$)S(O)$_2$N(C$_1$-C$_4$ alkyl)$_2$;

N(H)C(O)O—(C$_1$-C$_4$ alkyl);

N(CH$_3$)C(O)O—(C$_1$-C$_4$ alkyl);

N(H)S(O)$_2$O—(C$_1$-C$_4$ alkyl);

N(CH$_3$)S(O)$_2$O—(C$_1$-C$_4$ alkyl);

N(CH$_3$)C(S)NH—(C$_1$-C$_4$ alkyl);

N(CH$_3$)C(S)N(C$_1$-C$_4$ alkyl)$_2$;

N(CH$_3$)C(S)O—(C$_1$-C$_4$ alkyl);

N(H)C(S)NH$_2$;

NO$_2$;

CO$_2$H;

CO$_2$—(C$_1$-C$_4$ alkyl);

C(O)N(H)OH;

C(O)N(CH$_3$)OH:

C(O)N(CH$_3$)OH;

C(O)N(CH$_3$)O—(C$_1$-C$_4$ alkyl);

C(O)N(H)—(C$_1$-C$_4$ alkyl);

C(O)N(C$_1$-C$_4$ alkyl)$_2$;

C(S)N(H)—(C$_1$-C$_4$ alkyl);

C(S)N(C$_1$-C$_4$ alkyl)$_2$;

C(NH)N(H)—(C$_1$-C$_4$ alkyl);

C(NH)N(C$_1$-C$_4$ alkyl)$_2$;

C(NCH$_3$)N(H)—(C$_1$-C$_4$ alkyl);

C(NCH$_3$)N(C$_1$-C$_4$ alkyl)$_2$;

C(O)—(C$_1$-C$_4$ alkyl);

C(NH)—(C$_1$-C$_4$ alkyl);

C(NCH$_3$)—(C$_1$-C$_4$ alkyl);

C(NOH)—(C$_1$-C$_4$ alkyl);

C(NOCH$_3$)—(C$_1$-C$_4$ alkyl);

CN;

CHO;

CH$_2$OH;

CH$_2$O—(C$_1$-C$_4$ alkyl);

CH$_2$NH$_2$;

CH$_2$N(H)—(C$_1$-C$_4$ alkyl);

CH$_2$N(C$_1$-C$_4$ alkyl)$_2$;

aryl;

heteroaryl;

cycloalkyl; and heterocyclyl.

In some cases, a ring substituent may be shown as being connected to the ring by a bond extending from the center of the ring. The number of such substituents present on a ring is indicated in subscript by a number. Moreover, the substituent may be present on any available ring atom, the available ring atom being any ring atom which bears a hydrogen which the ring substituent may replace. For illustrative purposes, if variable R$^X$ were defined as being:

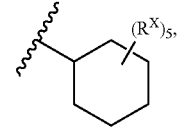

this would indicate a cyclohexyl ring bearing five R$^X$ substituents. The R$^X$ substituents may be bonded to any available ring atom. For example, among the configurations encompassed by this are configurations such as:

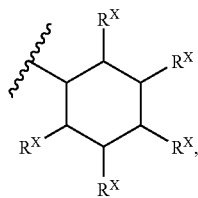 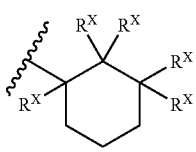

These configurations are illustrative and are not meant to limit the scope of the invention in any way.

When cyclic ring systems are illustrated with cycles or fragment of cycles in the formula, it is meant that the bridge atom connecting the cyclic ring systems with an the substituent (e.g. another ring) can be a carbon or nitrogen atom. For illustrative purposes, if the fragment Q$^X$ were defined as being a ring, wherein two adjacent atoms are substituted to form an additional 6-membered ring:

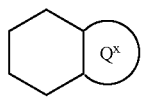

this would indicate that e.g. the following structures are possible:

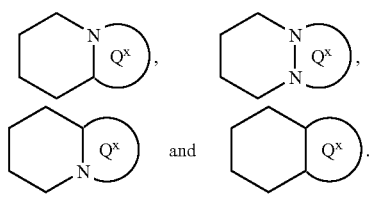

Biological Activity

The inhibiting activity towards different metalloproteases of the heterocyclic metalloprotease inhibiting compounds of the present invention may be measured using any suitable assay known in the art. A standard in vitro assay for measuring the metalloprotease inhibiting activity is described in Examples 1700 to 1704.

The heterocyclic metalloprotease inhibiting compounds of the invention have an MMP-13 inhibition activity ($IC_{50}$ MMP-13) ranging from below 0.1 nM to about 20 μM, and typically, from about 1 nM to about 1 μM. Heterocyclic metalloprotease inhibiting compounds of the invention desirably have an MMP inhibition activity ranging from below 0.2 nM to about 20 nM. Examples of heterocyclic metalloprotease inhibiting compounds of the invention that have an MMP-13 activity lower than 100 nM are Example 1, 1/1 and 1/4. An Examples ranging from 100 nM to 20 μM is Example 1/2.

The synthesis of metalloprotease inhibiting compounds of the invention and their biological activity assay are described in the following examples which are not intended to be limiting in any way.

General

Suitable cyclic systems $Q^2$ in Formula (I) can be prepared as described previously in our company, e.g. WO2006/128184 or US2007/0155738. They can be coupled e.g. via the standard EDCI/HOAt/base procedure to the amine building blocks described below.

EXAMPLES AND METHODS

All reagents and solvents were obtained from commercial sources and used without further purification. Proton spectra ($^1$H-NMR) were recorded on a 250 MHz NMR spectrometer in deuterated solvents. Purification by column chromatography was performed using silica gel, grade 60, 0.06-0.2 mm (chromatography) or silica gel, grade 60, 0.04-0.063 mm (flash chromatography) and suitable organic solvents as indicated in specific examples. Preparative thin layer chromatography was carried out on silica gel plates with UV detection.

Preparative Examples are directed to intermediate compounds useful in preparing the compounds of the present invention.

Preparative Example 1

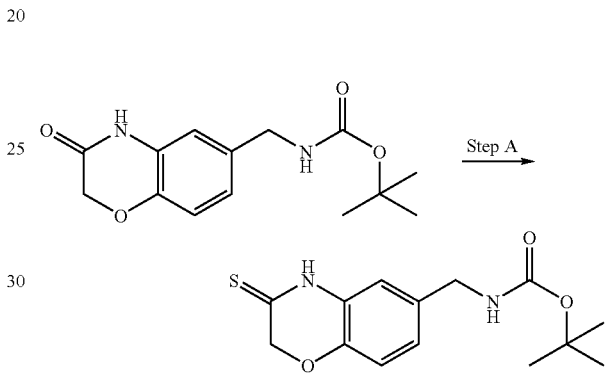

Step A

To a solution of the starting material (380 mg) (synthesis as described in WO2006/128184) in dry THF was added Lawesson's reagent (660 mg) and the mixture was stirred for 4 h and then concentrated. The remaining residue was dissolved in EtOAc, washed subsequently with 10% aqueous citric acid, saturated aqueous NaHCO$_3$ and brine, dried (MgSO$_4$), filtered, concentrated and purified by chromatography (silica, cyclohexane/EtOAc 85:15 to 8:2) to afford the title compound as a colourless solid (312 mg, 78%). [MNa]$^+$=317.

Preparative Example 1a

Following a similar procedure as described in the Preparative Example 1, except using the educt indicated in Table I.1 below, the following compound was prepared.

TABLE I.1

| Prep. Ex. # | educt | product | yield |
|---|---|---|---|
| 1a | (structure) | (structure) | 87%<br>[MH]$^+$ = 244/46 |

Preparative Example 2

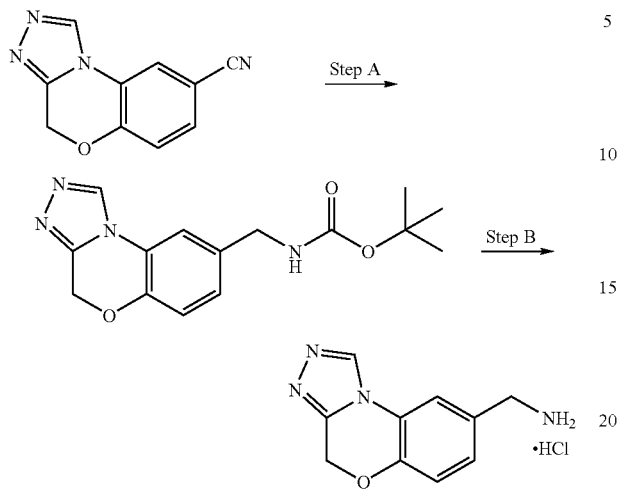

Step A

To an ice cooled solution of the title compound from Preparative Example 9 (100 mg) in dry MeOH were added di-tert-butyl dicarbonate (300 mg) and $NiCl_2.6H_2O$ (20 mg), followed by the careful portionwise addition of $NaBH_4$ (120 mg). The resulting black mixture was stirred for 10 min at 0-5° C. (ice bath), then the ice bath was removed and stirring at room temperature was continued for 2 h. Then diethylenetriamine was added and the mixture was concentrated to dryness. The remaining residue was suspended in EtOAc, washed subsequently with 10% aqueous citric acid, saturated aqueous $NaHCO_3$ and brine, dried ($MgSO_4$), filtered, concentrated and purified by flash chromatography ($CH_2Cl_2$/MeOH 95:5 to 9:1) to afford the title compound as a colourless solid. $[MNa]^+=324$.

Step B

The title compound from the Step A above was stirred in a 4M solution of HCl in 1,4-dioxane (10 mL) at room temperature for 4 h and then concentrated to afford the title compound (79 mg, 66% over two steps) as a colourless solid. $[M-NH_2C]^+=186$, $[M-Cl]^+=203$.

Preparative Example 2a

Following a similar procedure as described in the Preparative Example 2, Step A, except using the educt indicated in Table I.2 below, the following compound was prepared.

Preparative Example 3

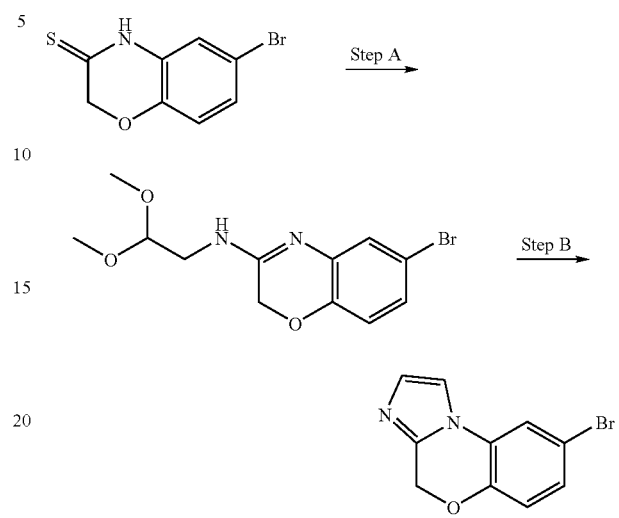

Step A

The title compound from Preparative Example 1a (387 mg), 2-aminoethyldimethylacetal (850 mg) in dry methanol (30 mL) was added $^t$butylperoxide (1 mL) and the mixture was stirred for 2 h at room temperature. Then a aqueous solution of sodium sulfite was added and the mixture was concentrated, diluted with ethyl acetate and washed with 1% citric acid and brine. The organic phase was separated, dried, concentrated and used without further purification. $[MH]^+=315/317$

Step B

The title compound from the Step A above was stirred in 3N HCl (20 mL) and isopropanol (60 mL) under reflux for 2 h, evaporated and diluted with water, filtered and dried to afford the title compound (228 mg, 57% over two steps) as an off-white solid, which was used without further purification

Preparative Examples 4a to 4e

Following a similar procedure as described in the Preparative Example 2, Step B except using the educt indicated in Table I.4 below, the following compounds were prepared.

TABLE I.2

| Prep. Ex. # | educt | product | yield |
|---|---|---|---|
| 2a | ![imidazo-benzoxazine-CN] | ![imidazo-benzoxazine-CH2NHBoc] | n.d. $[MH]^+ = 324$ |

TABLE I.4
| Prep. Ex. # | educt | product | yield |
|---|---|---|---|
| 4a | | | quant. [M-Cl]⁺ = 220 |
| 4b | | | quant. [M-Cl]⁺ = 194 |
| 4c | | | quant. [M-Cl]⁺ = 200 |
| 4d | | | quant. [M-Cl]⁺ = 194 |
| 4e | | | n.d. [M-Cl]⁺ = 202 |
Preparative Example 5
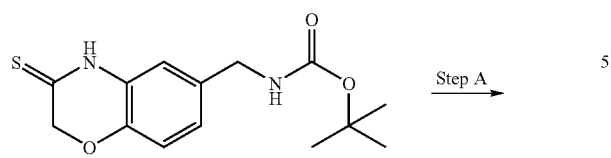
Step A
The title compound from the Preparative Example 1 (123 mg) was treated as described in Monatsh. Chem. 1989, 120, 81-84 to afford the title compound as a colourless solid (120 mg, 89%). [MNa]⁺=342.
Preparative Example 6
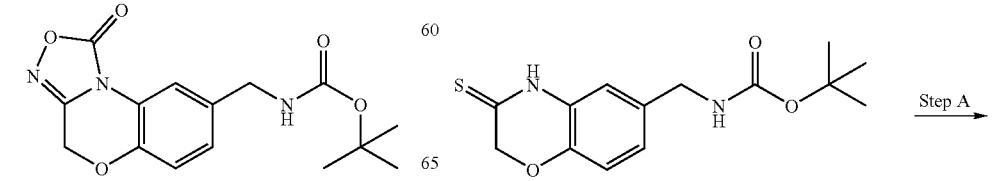

-continued

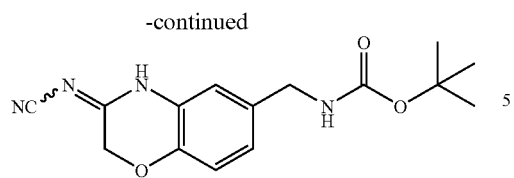

Step A

A suspension of the title compound from Preparative Example 1 (48 mg), cyanamide (80 mg), NEt₃ (20 μL) in dry MeOH (10 mL) was stirred at 60° C. overnight, evaporated, absorbed on silica and purified by flash chromatography (cyclohexane/ethyl acetate 6:4) to give the title compound (41 mg) as a colorless solid. [MNa]⁺=325.

Preparative Example 7

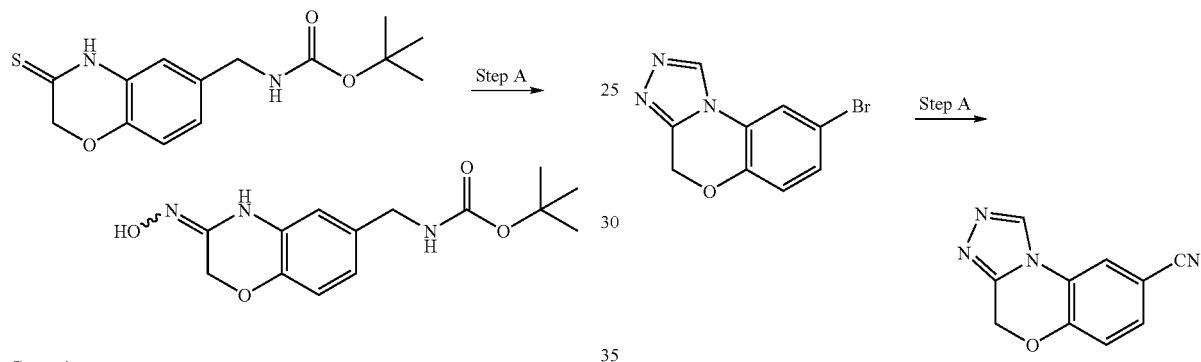

Step A

A suspension of the title compound from Preparative Example 1 (81 mg), HONH₂.HCl (60 mg), NEt₃ (100 μL) in dry MeOH (10 mL) was stirred at room temperature overnight, evaporated, diluted with EtOAc and washed with water and brine, dried and evaporated to give the title compound (90 mg, quant.) as a colourless solid. [MNa]⁺=316.

Preparative Example 8

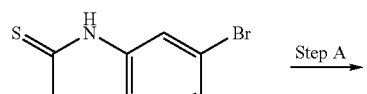

-continued

Step A

A solution of title compound the from Preparative Example 1a above (164 mg) and formylhydrazine (50 mg) in butanol was heated under microwave irradiation to 160° C. for 3 h, absorbed on silica and purified by flash chromatography (silica, CH₂Cl₂/methanol 98:2 to 95:5) to afford the title compound as a colourless solid (129 mg, 76%). [MH]⁺=252/54.

Preparative Example 9

Step A

A mixture of the title compound from the Preparative Example 8 (125 mg), Zn(CN)₂ (44 mg) and Pd(PPh₃)₄ (40 mg) in dry DMF (10 mL) was degassed and heated at 85° C. under an argon atmosphere overnight. The mixture was concentrated, diluted with 1N HCl, sonificated, filtered and washed with water, few methanol and then pentane to afford the title compound (100 mg, quant.) as a colourless solid. [MH]⁺=199.

Examples 9a

Following a similar procedure as described in the Example 9 except using bromide indicated in Table II.9 below, the following compound was prepared.

TABLE II.3

| Prep. Ex. # | educt | product | yield |
|---|---|---|---|
| 9a | | | n.d. [MH]⁺ = 198 |

Example 1

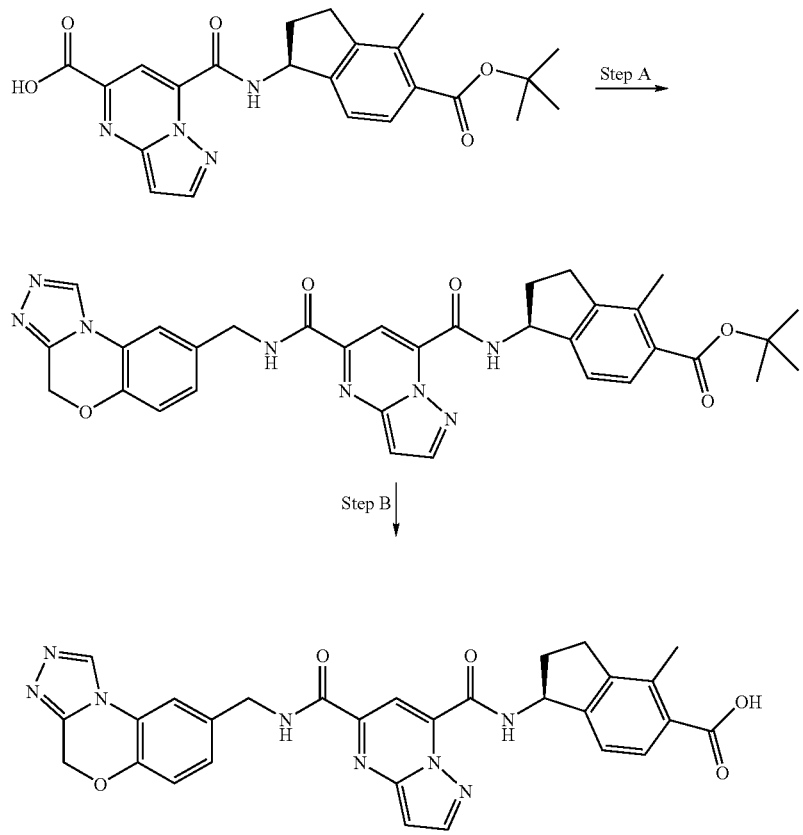

Step A

To a solution of the acid derivative (38 mg) (synthesis described in WO2006/128184), the amine from the Preparative Example 2, Step B above (25 mg), EDCI (~2 eq.) and HOAt (1 eq.) in DMF (10 mL) was added N-methylmorpholine (30 µL). The mixture was stirred overnight and then concentrated. The remaining residue was suspended in 10% aqueous citric acid and the residue was filtered to afford the title compound as a yellow solid, which was used without further purification in the next step. [MNa]$^+$=643.

Step B

The intermediate from Step A above was stirred in formic acid for 4 h and then evaporated. The remaining residue was suspended in 10% aqueous citric acid and the residue was filtered to afford the title compound as a yellow solid (37 mg, 75% over two steps). [MH]$^+$=565.

Examples 1/1 to 1/3

Following a similar procedure as described in the Example 3 except using the amines and acids indicated in Table II.1 below, the following compounds were prepared.

TABLE II.1

| Ex. # | amine, acid | product | yield |
|---|---|---|---|
| 1/1 | | | 4% [MH]$^+$ = 557 |

TABLE II.1-continued
| Ex. # | amine, acid | product | yield |
|---|---|---|---|
| 1/2 | 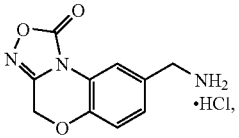 | 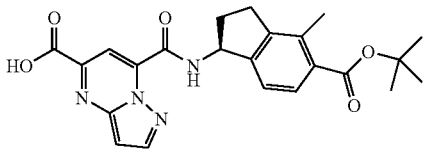 | 78% [MH]⁺ = 582 |
| 1/3 | 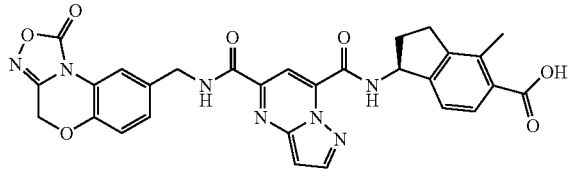 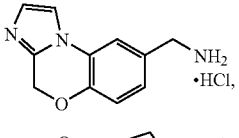 | 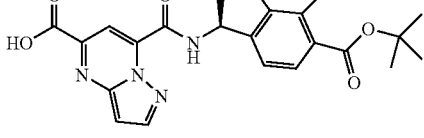 | 46% [MH]⁺ = 564 |
Examples 2/1 to 2/8
If one were to follow a similar procedure as described in the Example 1 except using the amines and acids indicated in Table II.2 below, the following compounds could be prepared.
TABLE II.2
| Ex. # | amine, acid | product |
|---|---|---|
| 2/1 | 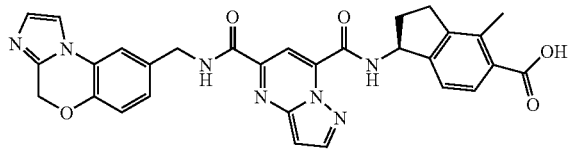 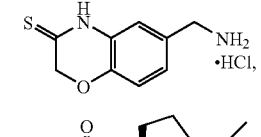 | 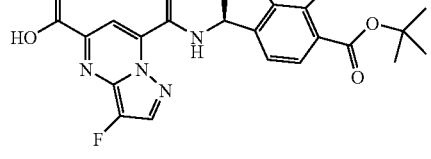 |
| 2/2 | 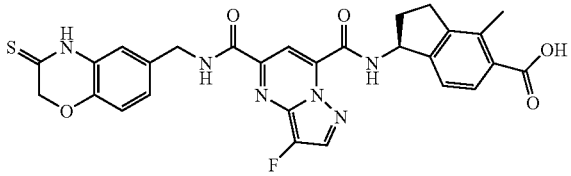 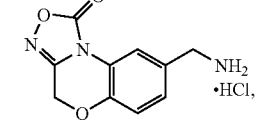 | 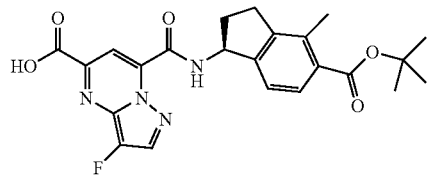 |

TABLE II.2-continued
| Ex. # | amine, acid | product |
|---|---|---|
| 2/3 | 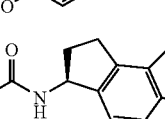 | 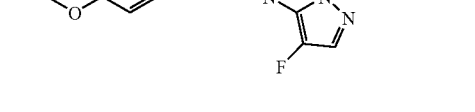 |
| 2/4 | 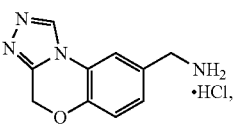 | 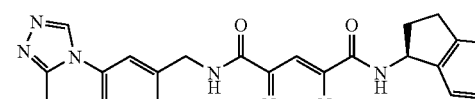 |
| 2/5 | 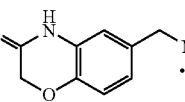 | 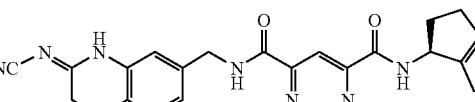 |
| 2/6 | 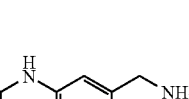 | 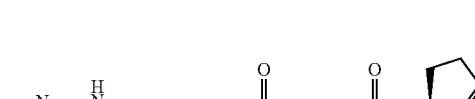 |

TABLE II.2-continued
| Ex. # | amine, acid | product |
|---|---|---|
| 2/7 | 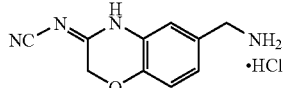 | 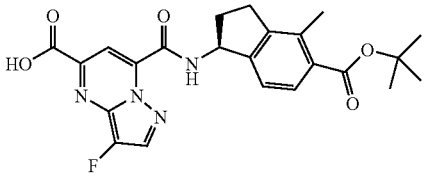 |
| 2/8 | 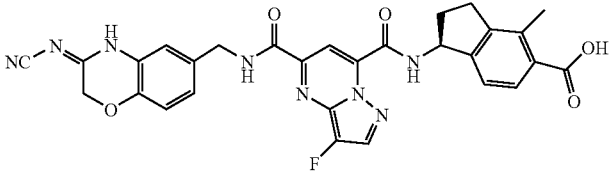 | 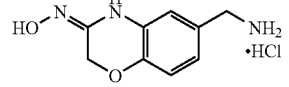 |
Examples 3/1 to 3/6
If one were to follow a similar procedure as described in the Example 1, Step A except using the amines and acids indicated in Table II.3 below, the following compounds could be prepared.
TABLE II.3
| Ex. # | amine, acid | product |
|---|---|---|
| 3/1 | 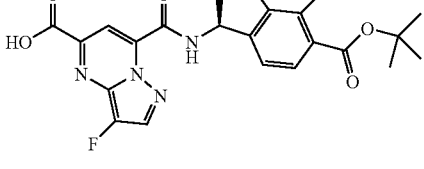<br>Prep. Ex. 371 of US US2007/0155738 | 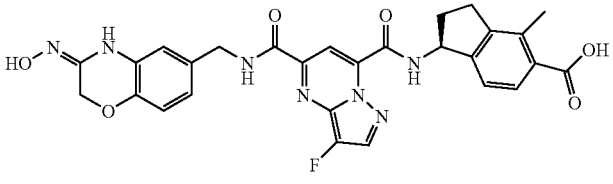 |

TABLE II.3-continued
| Ex. # | amine, acid | product |
|---|---|---|
| 3/2 | 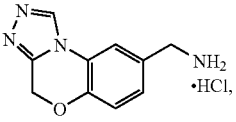 | 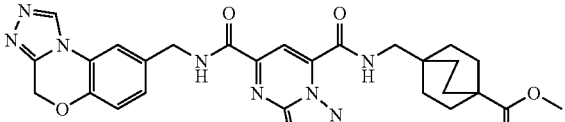 |
| 3/3 | 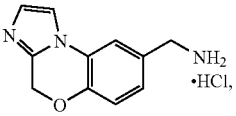<br>Prep. Ex. 372 of US US2007/0155738 | 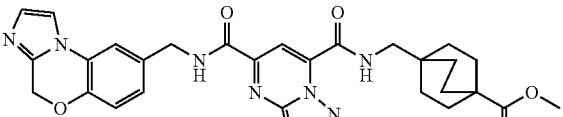 |
| 3/4 | 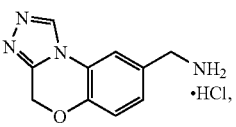 | 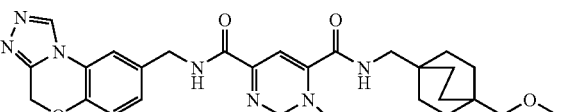 |
| 3/5 | 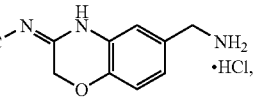 | 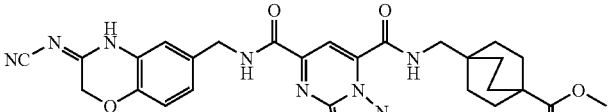 |

TABLE II.3-continued

| Ex. # | amine, acid | product |
|---|---|---|
| 3/6 | [structure: hydroxyimino-benzoxazine-methanamine·HCl and pyrazolo-carboxylic acid with bicyclic methyl ester] | [structure: bis-amide product with hydroxyimino-benzoxazine and bicyclic methyl ester linked through pyrazolopyrimidine dicarboxamide] |

Examples 4/1 to 4/6

If one were to follow a similar procedure as described in the Example 314 in US2007/0155738, except using the ester indicated in Table II.4 below, the following compounds could be prepared.

TABLE II.4

| Ex. # | ester |
|---|---|
| 4/1 | [structure: imidazo-benzoxazine linked via methylene-amide to fluoro-pyrazolopyrimidine dicarboxamide to bicyclic methyl ester] |
| 4/2 | [structure: triazolo-benzoxazine linked via methylene-amide to fluoro-pyrazolopyrimidine dicarboxamide to bicyclic methyl ester] |
| 4/3 | [structure: imidazo-benzoxazine linked via methylene-amide to pyrazolopyrimidine dicarboxamide to bicyclic methyl ester] |
| 4/4 | [structure: triazolo-benzoxazine linked via methylene-amide to pyrazolopyrimidine dicarboxamide to bicyclic methyl ester] |

TABLE II.4-continued

| Ex. # | product |
|---|---|
| 4/5 | (structure) |
| 4/6 | (structure) |

| Ex. # | product |
|---|---|
| 4/1 | (structure) |
| 4/2 | (structure) |
| 4/3 | (structure) |
| 4/4 | (structure) |
| 4/5 | (structure) |

TABLE II.4-continued

4/6

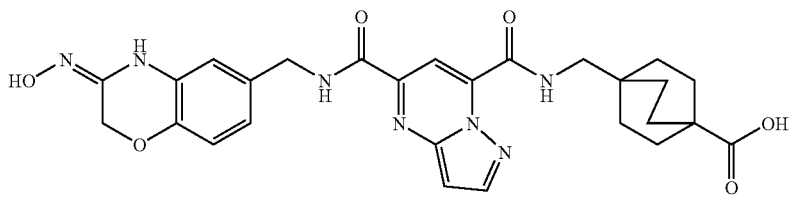

Example 1700

Assay for Determining MMP-13 Inhibition

The typical assay for MMP-13 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 µL aliquots. 10 µL of a 50 nM stock solution of catalytic domain of MMP-13 enzyme (produced by Alantos or commercially available from Invitek (Berlin), Cat.# 30100812) is added to the compound solution. The mixture of enzyme and compound in assay buffer is thoroughly mixed and incubated for 10 min at room temperature. Upon the completion of incubation, the assay is started by addition of 40 µL of a 12.5 µM stock solution of MMP-13 fluorescent substrate (Calbiochem, Cat. No. 444235). The time-dependent increase in fluorescence is measured at the 320 nm excitation and 390 nm emission by automatic plate multireader. The $IC_{50}$ values are calculated from the initial reaction rates.

Example 1701

Assay for Determining MMP-3 Inhibition

The typical assay for MMP-3 activity is carried out in assay buffer comprised of 50 mM MES, pH 6.0, 10 mM $CaCl_2$ and 0.05% Brij-35. Different concentrations of tested compounds are prepared in assay buffer in 50 µL aliquots. 10 µL of a 100 nM stock solution of the catalytic domain of MMP-3 enzyme (Biomol, Cat. No. SE-109) is added to the compound solution. The mixture of enzyme and compound in assay buffer is thoroughly mixed and incubated for 10 min at room temperature. Upon the completion of incubation, the assay is started by addition of 40 µL of a 12.5 µM stock solution of NFF-3 fluorescent substrate (Calbiochem, Cat. No. 480455). The time-dependent increase in fluorescence is measured at the 330 nm excitation and 390 nm emission by an automatic plate multireader. The $IC_{50}$ values are calculated from the initial reaction rates.

Example 1702

Assay for Determining MMP-8 Inhibition

The typical assay for MMP-8 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 µL aliquots. 10 µL of a 50 nM stock solution of activated MMP-8 enzyme (Calbiochem, Cat. No. 444229) is added to the compound solution. The mixture of enzyme and compound in assay buffer is thoroughly mixed and incubated for 10 min at 37° C. Upon the completion of incubation, the assay is started by addition of 40 µL of a 10 µM stock solution of OmniMMP fluorescent substrate (Biomol, Cat. No. P-126). The time-dependent increase in fluorescence is measured at the 320 nm excitation and 390 nm emission by an automatic plate multireader at 37° C. The $IC_{50}$ values are calculated from the initial reaction rates.

Example 1703

Assay for Determining MMP-12 Inhibition

The typical assay for MMP-12 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 µL aliquots. 10 µL of a 50 nM stock solution of the catalytic domain of MMP-12 enzyme (Biomol, Cat. No. SE-138) is added to the compound solution. The mixture of enzyme and compound in assay buffer is thoroughly mixed and incubated for 10 min at room temperature. Upon the completion of incubation, the assay is started by addition of 40 µL of a 12.5 µM stock solution of OmniMMP fluorescent substrate (Biomol, Cat. No. P-126). The time-dependent increase in fluorescence is measured at the 320 nm excitation and 390 nm emission by automatic plate multireader at 37° C. The $IC_{50}$ values are calculated from the initial reaction rates.

Example 1704

Assay for Determining Aggrecanase-1 Inhibition

The typical assay for aggrecanase-1 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 µL aliquots. 10 µL of a 75 nM stock solution of aggrecanase-1 (Invitek) is added to the compound solution. The mixture of enzyme and compound in assay buffer is thoroughly mixed. The reaction is started by addition of 40 µL of a 250 nM stock solution of aggrecan-IGD substrate (Invitek) and incubation at 37° C. for exact 15 min. The reaction is stopped by addition of EDTA and the samples are analysed by using aggrecanase ELISA (Invitek, InviLISA, Cat. No. 30510111) according to the protocol of the supplier. Shortly: 100 µL of each proteolytic reaction are incubated in a pre-coated micro plate for 90 min at room temperature. After 3 times washing, antibody-peroxidase conjugate is added for 90 min at room temperature. After 5 times washing, the plate is incubated with TMB solution for 3 min at room temperature. The peroxidase reaction is stopped with sulfurous acid and the absorbance is red at 450 nm. The $IC_{50}$ values are calculated from the absorbance signal corresponding to residual aggrecanase activity.

What is claimed:

1. A compound having Formula (I):

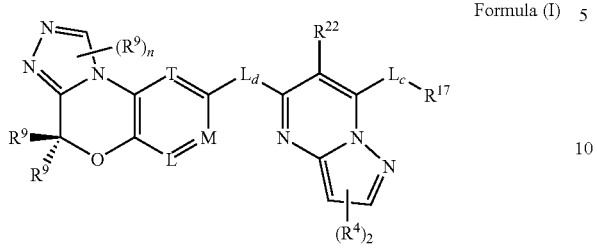

Formula (I)

wherein:

L, M and T are independently $CR^9$;

$R^4$ in each occurrence is independently selected from $R^{10}$, hydrogen, alkyl, cycloalkyl, heterocycloalkyl, aryl, heteroaryl, halo, haloalkyl, $CF_3$, $(C_0\text{-}C_6)$-alkyl-$COR^{10}$, $(C_0\text{-}C_6)$-alkyl-$OR^{10}$, $(C_0\text{-}C_6)$-alkyl-$NR^{10}R^{11}$, $(C_0\text{-}C_6)$-alkyl-$NO_2$, $(C_0\text{-}C_6)$-alkyl-$CN$, $(C_0\text{-}C_6)$-alkyl-$S(O)_yOR^{10}$, $(C_0\text{-}C_6)$-alkyl-$S(O)_yNR^{10}R^{11}$, $(C_0\text{-}C_6)$-alkyl-$NR^{10}CONR^{11}SO_2R^{30}$, $(C_0\text{-}C_6)$-alkyl-$S(O)_xR^{10}$, $(C_0\text{-}C_6)$-alkyl-$OC(O)R^{10}$, $(C_0\text{-}C_6)$-alkyl-$OC(O)NR^{10}R^{11}$, $(C_0\text{-}C_6)$-alkyl-$C(=NR^{10})NR^{10}R^{11}$, $(C_0\text{-}C_6)$-alkyl-$NR^{10}C(=NR^{11})NR^{10}R^{11}$, $(C_0\text{-}C_6)$-alkyl-$C(O)OR^{10}$, $(C_0\text{-}C_6)$-alkyl-$C(O)NR^{10}R^{11}$, $(C_0\text{-}C_6)$-alkyl-$C(O)NR^{10}SO_2R^{11}$, $(C_0\text{-}C_6)$-alkyl-$NR^{10}\text{—}C(O)R^{10}$, $(C_0\text{-}C_6)$-alkyl-$NR^{10}\text{—}C(O)OR^{10}$, $(C_0\text{-}C_6)$-alkyl-$NR^{10}\text{—}C(O)\text{—}NR^{10}R^{11}$, $(C_0\text{-}C_6)$-alkyl-$NR^{10}\text{—}S(O)_yNR^{10}R^{11}$, $(C_0\text{-}C_6)$-alkyl-$NR^{10}\text{—}S(O)_yR^{10}$, $O\text{—}(C_0\text{-}C_6)$-alkyl-aryl and $O\text{—}(C_0\text{-}C_6)$-alkyl-heteroaryl, wherein each $R^4$ group is optionally substituted by one or more $R^{14}$ groups;

$R^9$ in each occurrence is independently selected from $R^{10}$, hydrogen, alkyl, cycloalkyl, heterocycloalkyl, aryl, heteroaryl, halo, $CHF_2$, $CF_3$, $OR^{10}$, $SR^{10}$, $COOR^{10}$, $CH(CH_3)CO_2H$, $(C_0\text{-}C_6)$-alkyl-$COR^{10}$, $(C_0\text{-}C_6)$-alkyl-$OR^{10}$, $(C_0\text{-}C_6)$-alkyl-$NR^{10}R^{11}$, $(C_0\text{-}C_6)$-alkyl-$NO_2$, $(C_0\text{-}C_6)$-alkyl-$CN$, $(C_0\text{-}C_6)$-alkyl-$S(O)_yOR^{10}$, $(C_0\text{-}C_6)$-alkyl-$P(O)_2OH$, $(C_0\text{-}C_6)$-alkyl-$S(O)_yNR^{10}R^{11}$, $(C_0\text{-}C_6)$-alkyl-$NR^{10}CONR^{11}SO_2R^{30}$, $(C_0\text{-}C_6)$-alkyl-$S(O)_xR^{10}$, $(C_0\text{-}C_6)$-alkyl-$OC(O)R^{10}$, $(C_0\text{-}C_6)$-alkyl-$OC(O)NR^{10}R^{11}$, $(C_0\text{-}C_6)$-alkyl-$C(=NR^{10})NR^{10}R^{11}$, $(C_0\text{-}C_6)$-alkyl-$NR^{10}C(=NR^{11})NR^{10}R^{11}$, $(C_0\text{-}C_6)$-alkyl-$NR^{10}C(=N\text{—}CN)NR^{10}R^{11}$, $(C_0\text{-}C_6)$-alkyl-$C(=N\text{—}CN)NR^{10}R^{11}$, $(C_0\text{-}C_6)$-alkyl-$NR^{10}C(=N\text{—}NO_2)NR^{10}R^{11}$, $(C_0\text{-}C_6)$-alkyl-$C(=N\text{—}NO_2)NR^{10}R^{11}$, $(C_0\text{-}C_6)$-alkyl-$C(O)OR^{10}$, $(C_0\text{-}C_6)$-alkyl-$C(O)NR^{10}R^{11}$, $(C_0\text{-}C_6)$-alkyl-$C(O)NR^{10}SO_2R^{11}$, $C(O)NR^{10}\text{—}(C_0\text{-}C_6)$-alkyl-heteroaryl, $C(O)NR^{10}\text{—}(C_0\text{-}C_6)$-alkyl-aryl, $S(O)_2NR^{10}\text{—}(C_0\text{-}C_6)$-alkyl-aryl, $S(O)_2NR^{10}\text{—}(C_0\text{-}C_6)$-alkyl-heteroaryl, $S(O)_2NR^{10}$-alkyl, $S(O)_2\text{—}(C_0\text{-}C_6)$-alkyl-aryl, $S(O)_2\text{—}(C_0\text{-}C_6)$-alkyl-heteroaryl, $(C_0\text{-}C_6)$-alkyl-$C(O)\text{—}NR^{11}\text{—}CN$, $O\text{—}(C_0\text{-}C_6)$-alkyl-$C(O)NR^{10}R^{11}$, $S(O)_x\text{—}(C_0\text{-}C_6)$-alkyl-$C(O)OR^{10}$, $S(O)_x\text{—}(C_0\text{-}C_6)$-alkyl-$C(O)NR^{10}R^{11}$, $(C_0\text{-}C_6)$-alkyl-$C(O)NR^{10}\text{—}(C_0\text{-}C_6)$-alkyl-$NR^{10}R^{11}$, $(C_0\text{-}C_6)$-alkyl-$NR^{10}\text{—}C(O)R^{10}$, $(C_0\text{-}C_6)$-alkyl-$NR^{10}\text{—}C(O)OR^{10}$, $(C_0\text{-}C_6)$-alkyl-$NR^{10}\text{—}C(O)\text{—}NR^{10}R^{11}$, $(C_0\text{-}C_6)$-alkyl-$NR^{10}\text{—}S(O)_yNR^{10}R^{11}$, $(C_0\text{-}C_6)$-alkyl-$NR^{10}\text{—}S(O)_yR^{10}$, $O\text{—}(C_0\text{-}C_6)$-alkyl-aryl and $O\text{—}(C_0\text{-}C_6)$-alkyl-heteroaryl, wherein each $R^9$ group is optionally substituted by one or more $R^{100}$ groups;

$R^{10}$ and $R^{11}$ in each occurrence are independently selected from hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted by one or more $R^{100}$ groups, or $R^{10}$ and $R^{11}$ when taken together with the nitrogen to which they are attached complete a 3- to 8-membered ring containing carbon atoms and optionally containing a heteroatom selected from O, $S(O)_x$, or $NR^{50}$ and which is optionally substituted by one or more $R^{100}$ groups;

$R^{14}$ is independently selected from hydrogen, alkyl, arylalkyl, cycloalkylalkyl, heteroarylalkyl, heterocyclylalkyl and halo, wherein alkyl, arylalkyl, cycloalkylalkyl, heteroarylalkyl and heterocyclylalkyl are optionally substituted by one or more $R^{100}$ groups;

$R^{17}$ is selected from $R^9$, alkenyl, alkynyl, bicycloalkyl, heterobicycloalkyl, spiroalkyl, spiroheteroalkyl, cycloalkyl fused aryl, heterocycloalkyl fused aryl, cycloalkyl fused heteroaryl, heterocycloalkyl fused heteroaryl or a bicyclic or tricyclic fused ring system, wherein at least one ring is partially saturated, and wherein each $R^{17}$ group is optionally substituted one or more $R^9$ groups;

$R^{22}$ is selected from hydrogen, hydroxy, halo, alkyl, cycloalkyl, alkoxy, alkenyl, alkynyl, $NO_2$, $NR^{10}R^{11}$, $CN$, $SR^{10}$, $SSR^{10}$, $PO_3R^{10}$, $NR^{10}NR^{10}R^{11}$, $NR^{10}N=CR^{10}R^{11}$, $NR^{10}SO_2R^{11}$, $C(O)OR^{10}$, $C(O)NR^{10}R^{11}$, $SO_2R^{10}$, $SO_2NR^{10}R^{11}$ and fluoroalkyl, wherein alkyl, cycloalkyl, alkoxy, alkenyl, alkynyl, and fluoroalkyl are optionally substituted by one or more $R^{100}$ groups;

$R^{30}$ is selected from alkyl and $(C_0\text{-}C_6)$-alkyl-aryl, wherein alkyl and aryl are optionally substituted by one or more $R^{100}$ groups;

$R^{50}$ in each occurrence is independently selected from hydrogen, alkyl, aryl, heteroaryl, $C(O)R^{80}$, $C(O)NR^{80}R^{81}$, $SO_2R^{80}$ and $SO_2NR^{80}R^{81}$, wherein alkyl, aryl, and heteroaryl are optionally substituted by one or more $R^{100}$ groups;

$R^{80}$ and $R^{81}$ in each occurrence are independently selected from hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted by one or more $R^{100}$ groups, or $R^{80}$ and $R^{81}$ when taken together with the nitrogen to which they are attached complete a 3- to 8-membered ring containing carbon atoms and optionally a heteroatom selected from O, $S(O)_x$, NH, and N(alkyl) and which is optionally substituted by one or more $R^{100}$ groups;

$L_c$ is selected from a single bond or an acyclic, straight or branched, saturated or unsaturated hydrocarbon chain having 1 to 10 carbon atoms, optionally containing 1 to 3 groups independently selected from —S—, —O—, $NR^{10}$—, —$NR^{10}CO$—, —$CONR^{10}$—, —$S(O)_x$—, —$SO_2NR^{10}$—, —$NR^{10}SO_2$—, $NR^{10}SO_2NR^{10}$—, —$NR^{10}CONR^{10}$—, —$OC(O)NR^{10}$—, —$NR^{10}C(O)O$—, which replace single carbon atoms, which in case that more than two carbon atoms are replaced are not adjacent, and wherein the hydrocarbon chain is optionally substituted by one or more $R^{100}$ groups;

$L_d$ is selected from a single bond or a straight or branched, saturated or unsaturated hydrocarbon chain having 1 to 10 carbon atoms, optionally containing 1 to 3 groups independently selected from —O—, —NR$^{10}$—, —S(O)$_x$—, —NR$^{10}$C(X$^1$)—, —C(X$^1$)NR$^{10}$—, —SO$_2$NR$^{10}$—, —NR$^{10}$SO$_2$—, —O—SO$_2$—, —SO$_2$—O—, —NR$^{10}$SO$_2$NR$^{10}$—, —NR$^{10}$C(X$^1$)NR$^{10}$—, —OC(X$^1$)NR$^{10}$—, —NR$^{10}$C(X$^1$)O—, —OC(X$^1$)—, —C(X$^1$)O—, which replace single carbon atoms, which in case that more than two carbon atoms are replaced are not adjacent, and wherein the hydrocarbon chain is optionally substituted by one or more R$^{100}$ groups;

wherein each said R$^{100}$ groups is independently selected from: B(OH)$_2$; B(O—(C$_1$-C$_4$)alkyl)$_2$; C$_1$-C$_4$ alkyl; C$_2$-C$_4$ alkenyl; C$_2$-C$_4$ alkynyl; CF$_3$; halo; OH; O—(C$_1$-C$_4$ alkyl); OCH$_2$F; OCHF$_2$; OCF$_3$; ONO$_2$; OC(O)—(C$_1$-C$_4$ alkyl); OC(O)—(C$_1$-C$_4$alkyl); OC(O)NH—(C$_1$-C$_4$ alkyl); OC(O)N(C$_1$-C$_4$ alkyl)$_2$; OC(S)NH—(C$_1$-C$_4$ alkyl); OC(S)N(C$_1$-C$_4$ alkyl)$_2$; SH; S—(C$_1$-C$_4$ alkyl); S(O)—(C$_1$-C$_4$ alkyl); S(O)$_2$—(C$_1$-C$_4$ alkyl); SC(O)—(C$_1$-C$_4$ alkyl); SC(O)O—(C$_1$-C$_4$ alkyl); NH$_2$; N(H)—(C$_1$-C$_4$ alkyl); N(C$_1$-C$_4$ alkyl)$_2$; N(H)C(O)—(C$_1$-C$_4$ alkyl); (CH$_3$)C(O)—(C$_1$-C$_4$ alkyl); N(H)C(O)—CF$_3$; N(CH$_3$)C(O)—CF$_3$; N(H)C(S)—(C$_1$-C$_4$ alkyl); N(CH$_3$)C(S)—(C$_1$-C$_4$ alkyl); N(H)S(O)$_2$—(C$_1$-C$_4$ alkyl); N(H)C(O)NH$_2$; N(H)C(O)NH—(C$_1$-C$_4$ alkyl); N(CH$_3$)C(O)NH—(C$_1$-C$_4$ alkyl); N(H)C(O)N(C$_1$-C$_4$ alkyl)$_2$; N(CH$_3$)C(O)N(C$_1$-C$_4$alkyl)$_2$; N(H)S(O)$_2$NH$_2$); N(H)S(O)$_2$NH—(C$_1$-C$_4$ alkyl); N(CH$_3$)S(O)$_2$NH—(C$_1$-C$_4$ alkyl); N(H)S(O)$_2$N(C$_1$-C$_4$ alkyl)$_2$; N(CH$_3$)S(O)$_2$ N(C$_1$-C$_4$ alkyl)$_2$; N(H)C(O)O—(C$_1$-C$_4$ alkyl); N(CH$_3$)C(O)O—(C$_1$-C$_4$ alkyl); N(H)S(O)$_2$$^O$—(C$_1$-C$_4$ alkyl); N(CH$_3$)S(O)$_2$$^O$—(C$_1$-C$_4$ alkyl); N(CH$_3$)C(S)NH—(C$_1$-C$_4$ alkyl); N(CH$_3$)C(S)N(C$_1$-C$_4$ alkyl)$_2$; N(CH$_3$)C(S)O—(C$_1$-C$_4$ alkyl); N(H)C(S)NH$_2$; NO$_2$; CO$_2$H; CO$_2$—(C$_1$-C$_4$ alkyl); C(O)N(H)OH; C(O)N(CH$_3$)OH: C(O)N(CH$_3$)OH; C(O)N(CH$_3$)O—(C$_1$-C$_4$ alkyl); C(O)N(H)—(C$_1$-C$_4$ alkyl); C(O)N(C$_1$-C$_4$ alkyl)$_2$; C(S)N(H)—(C$_1$-C$_4$ alkyl); C(S)N(C$_1$-C$_4$ alkyl)$_2$; C(NH)N(H)—(C$_1$-C$_4$ alkyl); C(NH)N(C$_1$-C$_4$ alkyl)$_2$; C(NCH$_3$)N(H)—(C$_1$-C$_4$alkyl); C(NCH$_3$)N(C$_1$-C$_4$ alkyl)$_2$; C(O)—(C$_1$-C$_4$ alkyl); C(NH)—(C$_1$-C$_4$ alkyl); C(NCH$_3$)—(C$_1$-C$_4$ alkyl); C(NOH)—(C$_1$-C$_4$ alkyl); C(NOCH$_3$)—(C$_1$-C$_4$ alkyl); CN; CHO; CH$_2$OH; CH$_2$O—(C$_1$-C$_4$ alkyl); CH$_2$NH$_2$; CH$_2$N(H)—(C$_1$-C$_4$ alkyl); CH$_2$N(C$_1$-C$_4$ alkyl)$_2$; aryl; heteroaryl; cycloalkyl; and heterocyclyl;

X$^1$ is independently selected from O, S, NR$^{10}$, NOR$^{10}$, N—CN, NCOR$^{10}$, N—NO$_2$, and N—SO$_2$R$^{10}$;

x is independently selected from 0 to 2;

y is selected from 1 and 2 n is selected from 0 to 2; and

N-oxides, pharmaceutically acceptable salts, racemic mixtures and stereoisomers thereof.

2. The compound of claim 1 having the following formula:

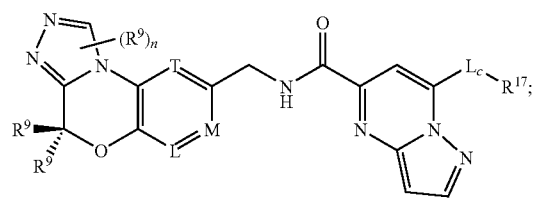

wherein:

L, M and T are independently CR$^9$.

3. The compound of claim 2 selected from:

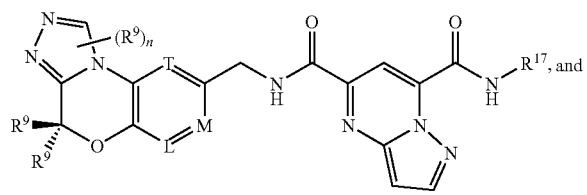

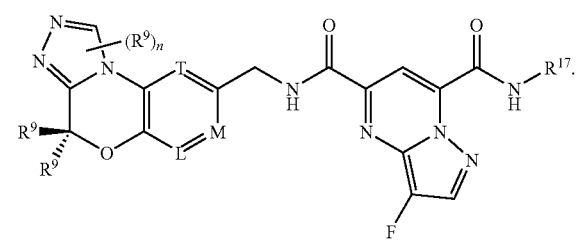

4. The compound of claim 3 selected from:

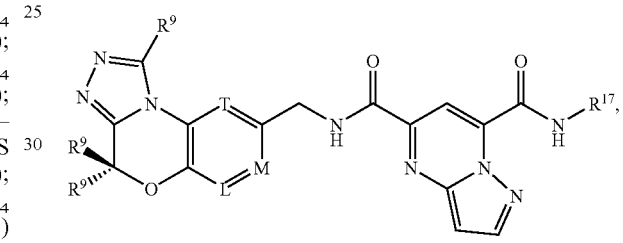

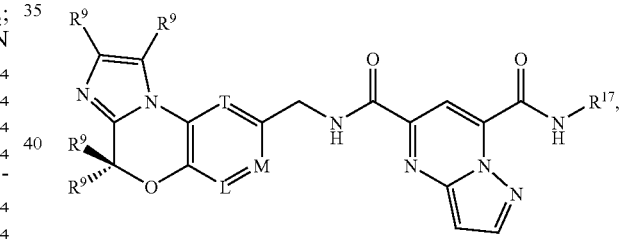

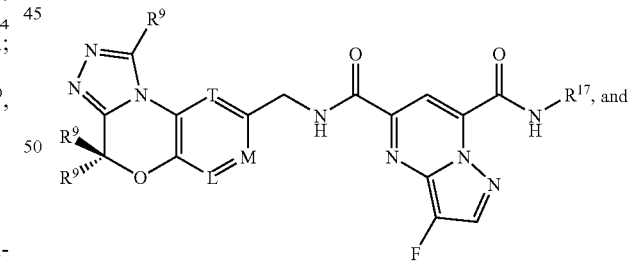

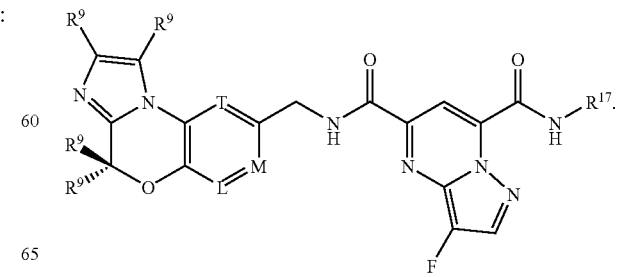

5. The compound of claim 3 wherein $R^{17}$ is selected from:

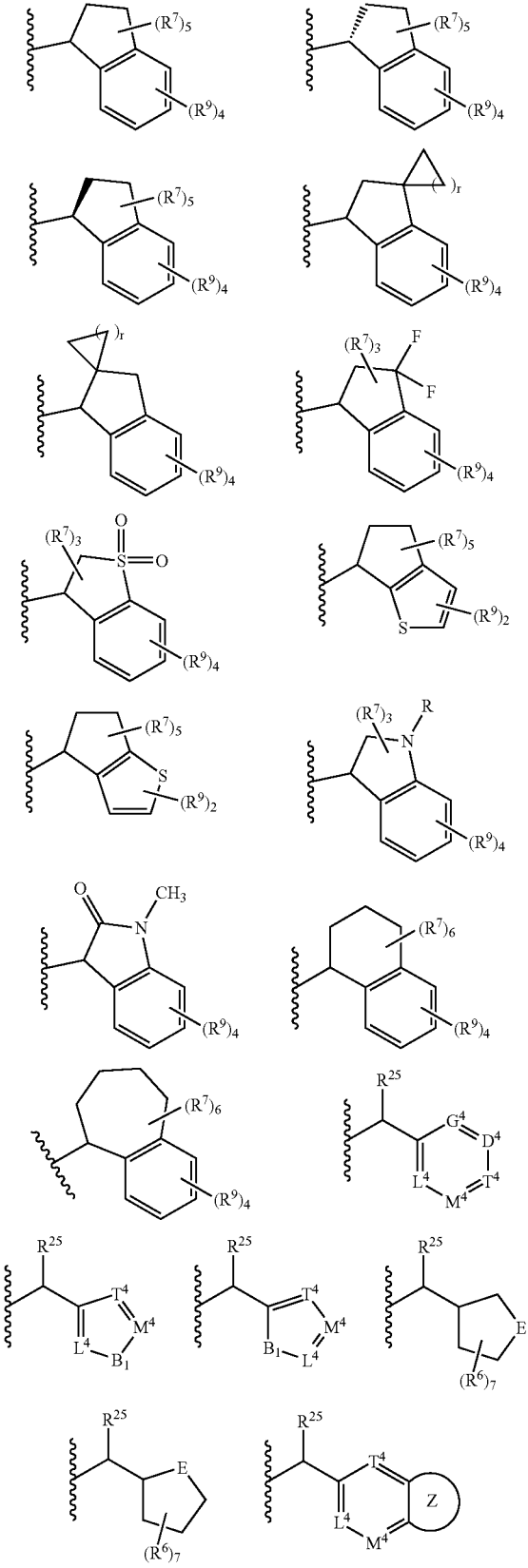
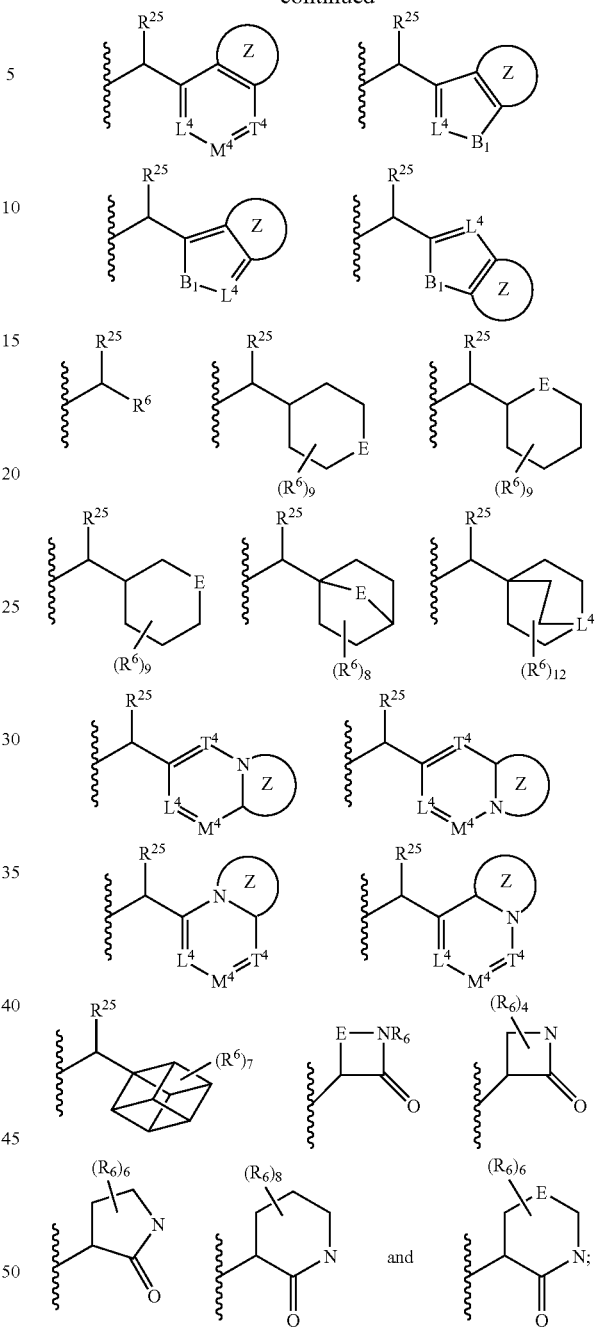

wherein:

R is selected from $C(O)NR^{10}R^{11}$, $COR^{10}$, $SO_2NR^{10}R^{11}$, $SO_2R^{10}$, $CONHCH_3$ and $CON(CH_3)_2$, wherein $C(O)NR^{10}R^{11}$, $COR^{10}$, $SO_2NR^{10}R^{11}$, $SO_2R^{10}$, $CONHCH_3$ and $CON(CH_3)_2$ are optionally substituted by one or more $R^{100}$ groups;

$R^5$ in each occurrence is independently selected from hydrogen, alkyl, $C(O)NR^{10}R^{11}$, aryl, arylalkyl, $SO_2NR^{10}R^{11}$ and $C(O)OR^{10}$, wherein alkyl, aryl and arylalkyl are optionally substituted by one or more $R^{100}$ groups;

$R^6$ is independently selected from $R^9$, alkenyl, alkynyl, cycloalkyl, heterocycloalkyl, bicycloalkyl, heterobicycloalkyl, spiroalkyl, spiroheteroalkyl, aryl, heteroaryl, $C(O)OR^{10}$, $CH(CH_3)CO_2H$, $(C_0\text{-}C_6)\text{-alkyl-}COR^{10}$, $(C_0\text{-}C_6)\text{-alkyl-}OR^{10}$, $(C_0\text{-}C_6)\text{-alkyl-}NR^{10}R^{11}$, $(C_0\text{-}C_6)\text{-alkyl-}NO_2$, $(C_0\text{-}C_6)\text{-alkyl-}CN$, $(C_0\text{-}C_6)\text{-alkyl-}S(O)_y$$OR^{10}$, $(C_0\text{-}C_6)\text{-alkyl-}P(O)_2OH$, $(C_0\text{-}C_6)\text{-alkyl-}S(O)_y$$NR^{10}R^{11}$, $(C_0\text{-}C_6)\text{-alkyl-}NR^{10}CONR^{11}SO_2R^{30}$, $(C_0\text{-}C_6)\text{-alkyl-}S(O)_xR^{10}$, $(C_0\text{-}C_6)\text{-alkyl-}OC(O)R^{10}$, $(C_0\text{-}C_6)\text{-alkyl-}OC(O)NR^{10}R^{11}$, $(C_0\text{-}C_6)\text{-alkyl-}C(=NR^{10})NR^{10}R^{11}$, $(C_0\text{-}C_6)\text{-alkyl-}NR^{10}C(=NR^{11})NR^{10}R^{11}$, $(C_0\text{-}C_6)\text{-alkyl-}NR^{10}C(=N\text{-}CN)NR^{10}R^{11}$, $(C_0\text{-}C_6)\text{-alkyl-}C(=N\text{-}CN)NR^{10}R^{11}$, $(C_0\text{-}C_6)\text{-alkyl-}NR^{10}C(=N\text{-}NO_2)NR^{10}R^{11}$, $(C_0\text{-}C_6)\text{-alkyl-}C(=N\text{-}NO_2)NR^{10}R^{11}$, $(C_0\text{-}C_6)\text{-alkyl-}C(O)OR^{10}$, $(C_0\text{-}C_6)\text{-alkyl-}C(O)NR^{10}R^{11}$, $(C_0\text{-}C_6)\text{-alkyl-}C(O)NR^{10}SO_2R^{11}$, $C(O)NR^{10}\text{---}(C_0\text{-}C_6)\text{-alkyl-heteroaryl}$, $C(O)NR^{10}\text{---}(C_0\text{-}C_6)\text{-alkyl-aryl}$, $S(O)_2NR^{10}\text{---}(C_0\text{-}C_6)\text{-alkyl-aryl}$, $S(O)_2NR^{10}\text{---}(C_0\text{-}C_6)\text{-alkyl-heteroaryl}$, $S(O)_2NR^{10}\text{-alkyl}$, $S(O)_2\text{---}(C_0\text{-}C_6)\text{-alkyl-aryl}$, $S(O)_2\text{---}(C_0\text{-}C_6)\text{-alkyl-heteroaryl}$, $(C_0\text{-}C_6)\text{-alkyl-}C(O)\text{---}NR^{11}\text{---}CN$, $O\text{---}(C_0\text{-}C_6)\text{-alkyl-}C(O)NR^{10}R^{11}$, $(C_0\text{-}C_6)\text{-alkyl-}C(O)NR^{10}\text{---}(C_0\text{-}C_6)\text{-alkyl-}NR^{10}R^{11}$, $(C_0\text{-}C_6)\text{-alkyl-}NR^{10}\text{---}C(O)R^{10}$, $(C_0\text{-}C_6)\text{-alkyl-}NR^{10}\text{---}C(O)OR^{10}$, $(C_0\text{-}C_6)\text{-alkyl-}NR^{10}\text{---}C(O)\text{---}NR^{10}R^{11}$, $(C_0\text{-}C_6)\text{-alkyl-}NR^{10}\text{---}S(O)_y NR^{10}R^{11}$, $(C_0\text{-}C_6)\text{-alkyl-}NR^{10}\text{---}S(O)_y R^{11}$, $O\text{---}(C_0\text{-}C_6)\text{-alkyl-aryl}$ and $O\text{---}(C_0\text{-}C_6)\text{-alkyl-heteroaryl}$, wherein each $R^6$ group is optionally substituted by one or more $R^{14}$ groups;

$R^7$ is independently selected from hydrogen, alkyl, cycloalkyl, halo, $R^4$ and $NR^{10}R^{11}$, wherein alkyl and cycloalkyl are optionally substituted by one or more $R^{100}$ groups, or optionally two $R^7$ groups together at the same carbon atom form =O, =S or =$NR^{10}$;

$R^{25}$ is independently selected from hydrogen, alkyl, cycloalkyl, $C(O)R^{10}$, $C(O)NR^{10}R^{11}$ and haloalkyl, wherein alkyl, cycloalkyl, and haloalkyl are optionally substituted by one or more $R^{100}$ groups;

$B_1$ is selected from $NR^{10}$, O and $S(O)_x$;

$D^4$, $G^4$, $L^4$, $M^4$, and $T^4$, are independently selected from $CR^6$ and N;

E is independently selected from a bond, $CR^{10}R^{11}$, O, $NR^5$, S, S=O, $S(=O)_2$, $C(=O)$, $N(R^{10})(C=O)$, $(C=O)N(R^{10})$, $N(R^{10})S(=O)_2$, $S(=O)_2N(R^{10})$, $C=N\text{---}OR^{11}$, $\text{---}C(R^{10}R^{11})C(R^{10}R^{11})\text{---}$, $\text{---}CH_2\text{---}W^1\text{---}$ and

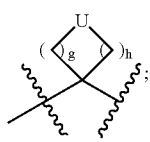

U is independently selected from $C(R^5R^{10})$, $NR^5$, O, S, S=O and $S(O)_2$;

$W^1$ is independently selected from O, $NR^5$, S, S=O, $S(=O)_2$, $N(R^{10})(C=O)$, $N(R^{10})S(=O)_2$ and $S(=O)_2N(R^{10})$;

Z is a 4- to 8-membered ring consisting of cycloalkyl, heterocycloalkyl or a 5- or 6-membered ring selected from aryl and heteroaryl, wherein cycloalkyl, heterocycloalkyl, aryl and heteroaryl are optionally substituted by one or more $R^{100}$ groups;

g and h are independently selected from 0-2; and r is selected from 1-4.

6. The compound according to claim 5, wherein $R^{17}$ is selected from:

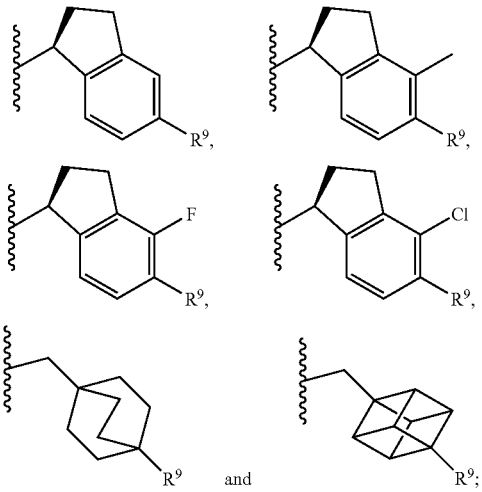

and wherein $R^9$ is selected from hydrogen, fluoro, halo, CN, alkyl, $CO_2H$,

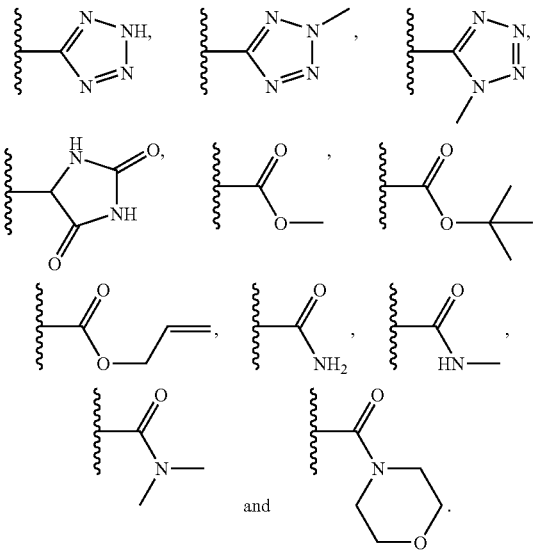

and

7. The compound according to claim 1 selected from:

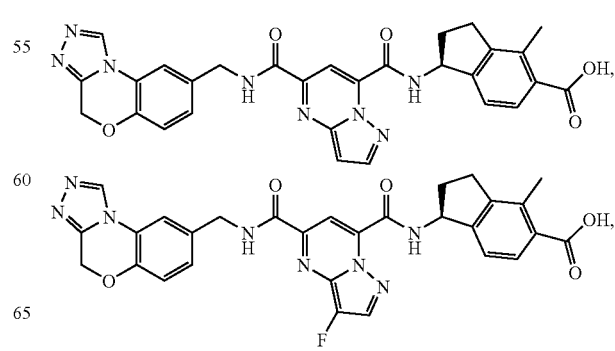

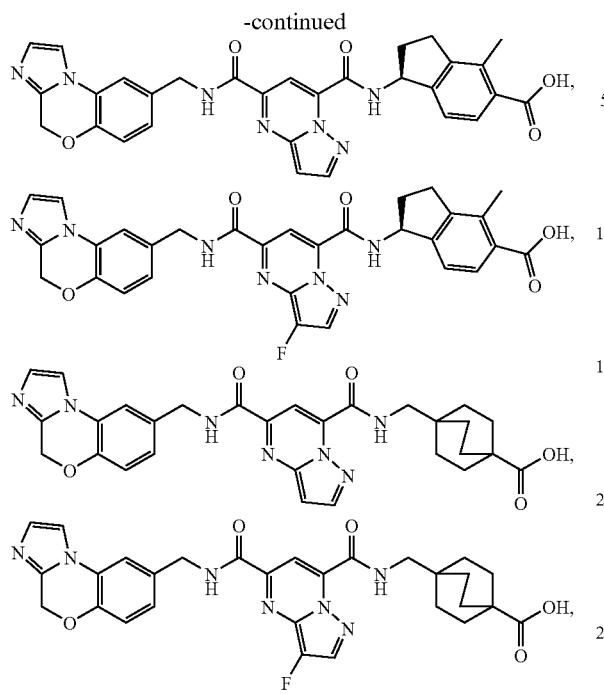
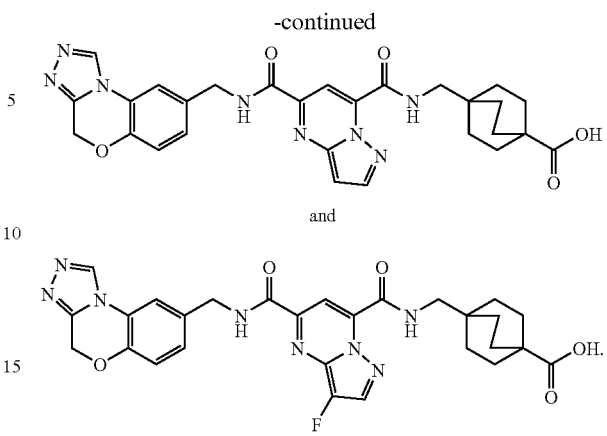
8. A pharmaceutical composition comprising an effective amount of a compound according to claim 1; and a pharmaceutically-acceptable carrier.
9. A method of treating rheumatoid arthritis or osteoarthritis comprising administering a therapeutically-effective amount of a compound according to claim 1.
* * * * *